United States Patent
Fülöp et al.

(10) Patent No.: US 10,660,789 B2
(45) Date of Patent: *May 26, 2020

(54) 1,4-DIHYDROPYRIDINE DERIVATIVES WITH HSP MODULATING ACTIVITY

(71) Applicant: Richter Gedeon NYRT., Budapest (HU)

(72) Inventors: Ferenc Fülöp, Szeged (HU); László Vígh, Szeged (HU); Zsolt Török, Szeged (HU); Botond Penke, Szeged (HU); Ibolya Horváth, Szeged (HU); Gábor Balogh, Budapest (HU); Sándor Bernáth, Telki (HU); Ákos Hunya, Szeged (HU)

(73) Assignee: RICHTER GEDEON NYRT., Budapest (HU)

(*) Notice: Subject to any disclaimer, the term of this patent is extended or adjusted under 35 U.S.C. 154(b) by 0 days.

This patent is subject to a terminal disclaimer.

(21) Appl. No.: 16/288,833

(22) Filed: Feb. 28, 2019

(65) Prior Publication Data

US 2019/0192336 A1  Jun. 27, 2019

Related U.S. Application Data

(63) Continuation of application No. 14/359,830, filed as application No. PCT/HU2012/000126 on Nov. 22, 2012, now Pat. No. 10,258,498.

(30) Foreign Application Priority Data

Nov. 24, 2011 (HU) .................... 1100646

(51) Int. Cl.
*A61K 31/4422* (2006.01)
*A61K 31/443* (2006.01)
*A61K 31/4436* (2006.01)
*C07D 211/86* (2006.01)
*C07D 405/04* (2006.01)
*C07D 409/04* (2006.01)
*A61F 7/00* (2006.01)
*C07D 401/06* (2006.01)
*C07D 401/10* (2006.01)
*C07D 211/90* (2006.01)
*A61K 31/4439* (2006.01)
*A61K 31/444* (2006.01)
*A61K 31/4545* (2006.01)
(Continued)

(52) U.S. Cl.
CPC .............. *A61F 7/00* (2013.01); *A61K 31/444* (2013.01); *A61K 31/4422* (2013.01); *A61K 31/4439* (2013.01); *A61K 31/4545* (2013.01); *A61K 31/475* (2013.01); *A61K 31/496* (2013.01); *A61K 31/5377* (2013.01); *A61K 31/55* (2013.01); *C07D 211/90* (2013.01); *C07D 401/06* (2013.01); *C07D 401/10* (2013.01); *C07D 401/14* (2013.01); *C07D 405/04* (2013.01); *C07D 409/04* (2013.01)

(58) Field of Classification Search
CPC .. C07D 211/86; C07D 405/04; C07D 409/04; A61K 31/443; A61K 31/4436
USPC .............. 514/356, 354, 336; 546/321, 283.4, 546/280.4
See application file for complete search history.

(56) References Cited

U.S. PATENT DOCUMENTS 5,234,935 A   8/1993 Behner et al.
5,432,185 A   7/1995 Behner et al.
(Continued)

FOREIGN PATENT DOCUMENTS

CN   101897705 A  * 12/2010
CN   101897705 A    12/2012
(Continued)

OTHER PUBLICATIONS

Ciocca, D., and S. Calderwood, "Heat shock proteins in cancer: diagnostic, prognostic, predictive, and treatment implications", Cell Stress & Chaperones (2005), 10(2), pp. 86-103. (Year: 2005).*
(Continued)

*Primary Examiner* — Matthew P Coughlin
*Assistant Examiner* — Sagar Patel
(74) *Attorney, Agent, or Firm* — Sterne, Kessler, Goldstein & Fox P.L.L.C.

(57) ABSTRACT

The invention provides 1,4-dihydropyridine derivatives of formula (I) wherein $R^1$ is optionally substituted $C_{6-24}$aryl group or 5 to 6 membered heteroaryl group comprising 1 to 3 nitrogen atoms or other heteroatoms like oxygen and sulphur, and combinations thereof; $R^2$ and $R^3$ are independently hydrogen or $C_{1-6}$alkyl group; $R^4$ and $R^5$ are independently hydrogen, $C_{1-6}$alkyl group optionally substituted with amino, mono- or di($C_{1-6}$alkyl)amino, or with 5 to 24 membered optionally fused heterocyclic ring attached by nitrogen and optionally comprising additional 1 to 3 N, O, S heteroatoms and optionally substituted with $C_{1-6}$alkyl group or $C_{1-6}$ alkoxy group; $R^6$ is $C_{1-6}$alkyl, $C_{3-7}$cycloalkyl, $C_{3-7}$cycloalkyl$C_{1-6}$alkyl or aryl$C_{1-6}$alkyl group; and stereoisomers including enantiomers, diastereomers, racemic mixtures, mixture of enantiomers and combination thereof, as well as polymorphs, pharmaceutically acceptable salts, solvates, esters and prodrugs thereof for use in the therapeutic or prophylactic treatment of a disorder mediated by heat shock proteins.

(I)

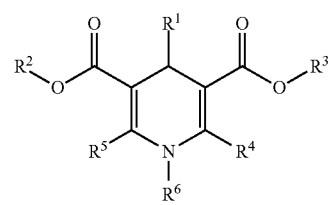

18 Claims, 5 Drawing Sheets

(51) Int. Cl.
  *A61K 31/475* (2006.01)
  *A61K 31/496* (2006.01)
  *A61K 31/5377* (2006.01)
  *A61K 31/55* (2006.01)
  *C07D 401/14* (2006.01)

(56) References Cited

U.S. PATENT DOCUMENTS

| | | | |
|---|---|---|---|
| 5,646,166 | A | 7/1997 | Urbahns et al. |
| 5,665,741 | A | 9/1997 | Urbahns et al. |
| 5,942,526 | A | 8/1999 | Urbahns et al. |
| 5,955,482 | A | 9/1999 | Urbahns et al. |
| 2007/0027194 | A1 | 2/2007 | Easterling et al. |
| 2014/0315893 | A1 | 10/2014 | Fulop et al. |

FOREIGN PATENT DOCUMENTS

| | | |
|---|---|---|
| DE | 44 30 094 A1 | 4/1996 |
| EP | 0 330 470 A2 | 8/1989 |
| EP | 0 533 504 A1 | 3/1993 |
| EP | 0 705 819 A1 | 4/1996 |
| EP | 0 717 036 A1 | 6/1996 |
| EP | 0 451 654 A2 | 10/1996 |
| EP | 1 055 672 A1 | 11/2000 |
| EP | 1 698 340 A1 | 9/2006 |
| WO | WO 99/01432 A1 | 1/1999 |
| WO | WO 03/086383 A1 | 10/2003 |
| WO | WO 2005/097118 A1 | 10/2005 |
| WO | WO 2010/003023 A2 | 1/2010 |

OTHER PUBLICATIONS

Gibbs, Frederic A., et al., "Regional hyperthermia in the treatment of cancer: a review," *Cancer Investigation*, 1985, 3(5):445-451.

Ciocca. D., et al., "Heat shock proteins in cancer: diagnostic, prognostic, predictive, and treatment implications," Cell Stress & Chaperones 10:86-103, Cell Stress Society International (2005).

Matsui, T., et al., "Bay w 9798 Inhibits Tumor Necrosis Factor-a-induced Vascular Cell Adhesion Molecule-1 Expression in Endothelial Cells by Suppressing Reactive Oxygen Species Generation," The Journal of international Medical Research 35:886-891, Field House Publishing (2007).

Ohsumi, k., et al., "N-Alkylated 1,4-Dihydropyridines: New Agents to Overcome Multidrug Resistance," Chem. Pharm. Bull 43:818-828, Pharmaceutical Society of Japan (1995).

Santoro, M., "Heat Shock Factors and the Control of the Stress Response," Biochem. Pharm. 59:55-63, Elsevier, Netherlands (2000).

Secchiero, P., et al., "Tumor necrosis factor (TNF)-related apoptosis-inducing ligand (TRAIL) and TNF-α promote the NF-κB dependent maturation of normal and leukemic myeloid cells," Journal of Leukocyte Bio. 74:223-232, (2003).

English language translation of Chinese Patent Publication CN101897705A, European Patent Office, espacenet database—worldwide (listed as document FP13 on the accompanying form PTO/SB/08a.

\* cited by examiner

1,4-DIHYDROPYRIDINE DERIVATIVES WITH HSP MODULATING ACTIVITY

BACKGROUND OF THE INVENTION

1. Technical Field of the Invention

The invention relates to partly new compounds which are useful as pharmaceuticals, to pharmaceutical and cosmetical compositions containing new compounds and to such compounds for the use in the treatment and prevention of pathophysiological conditions and diseases either mediated or influenced by heat shock proteins (Hsps) also termed stress proteins. More particularly the invention relates to certain 1,4-dihydropyridines with selective Hsp modulating activity both in vitro and in vivo, and to the use of such compounds in the field of the treatment and prevention of pathophysiological conditions mediated by Hsps, including for example neurodegenerative diseases, cancer, metabolic syndromes, diabetes, obesity, inflammation and skin diseases, as well as diseases and/or disorders that would benefit from altered Hsp function in various metabolic or environmental stress conditions and to pharmaceutical and cosmetical compositions comprising such compounds.

2. Description of the Prior Art

Heat shock proteins (Hsps) belong to functionally related proteins whose cellular amount changes when cells are exposed to elevated temperatures or other stresses (Goldberg et al., Nature, 426: 895-899, 2003) ranging from hypoxia, inflammation, or infections to environmental pollutants. Certain Hsps may also function as molecular chaperones under normal stress-free conditions by regulating the correct folding and function of numerous important cellular proteins.

Major heat-shock proteins are grouped according to their molecular weight (Hsp 100, Hsp 90, Hsp70, Hsp60, and the "small Hsps", sHsps).

Some members of the Hsp family are expressed at low to moderate levels in all organisms because of their essential role in protein maintenance. Due to their multiple and vital functions, Hsps play fundamental roles in the aetiology of several human diseases (Solti et al., Br. J. Pharmacol., 146: 769-780, 2005). For example aberrantly high levels of either the overall array of Hsps, or certain Hsp classes are characteristic in different cancer cells and the converse applies typically for type 2 diabetes, neurodegeneration, cardiovascular diseases or aging (Vigh et al.; Prog. Lipid Res., 44(5): 303-344, 2005 and Vigh et al.; Trends Biochem. Sci., 32: 357-363, 2007).

In order to highlight the mechanism of action of the different Hsp classes and to provide compounds moderating their activity and being suitable for drug development a large number of investigations have been undertaken over the last decade.

Hsp 70

The evolutionary conserved Hsp70 chaperone family and its co-chaperones with the exception of some archaea (Large et al., Biochem. Soc. Trans. 37: 46-51, 2009), are present in all ATP-containing compartments of living organisms (Macario et al., Genetics, 152:1277-1283, 1999). The functional Hsp70 chaperone network entails ATP-driven interactions among many diverse substrate-specific and less specific J-domain co-chaperones (49 in human) that target the fewer Hsp70 isoforms (Kampinga et al., Cell Stress Chaperones, 14:105-111, 2009) onto hundreds of protein substrates in the cell and are regulated by various nucleotide exchange factors such as glucose regulated protein E (GrpE) (Harrison, Cell Stress Chaperones 8:218-224, 2003), BAG (Kabbage et al., Cell Mol Life Sci., 65: 1390-1402, 2008), HspBP1 (Kabani et al., FEBS Lett., 531:339-342, 2002), and Hsp110 proteins (Shaner et al., Cell Stress Chaperones, 12:1-8, 2007). These networks are crucial to the co-translational folding of nascent polypeptides, the remodelling of native protein complexes, the transduction of cellular signals, the regulation of the cell cycle, proliferation and apoptosis (Jolly et al., J. Natl. Cancer Inst., 92:1564-1572, 2000), the regulation of the heat shock response, the unfolding and refolding of stress-denatured proteins, and the import of proteins into the mitochondria (De Los Rios et al., Proc Natl Acad Sci USA, 103:6166-6171, 2006), chloroplasts (Shi et al., Plant Cell, 22:205-220, 2010), and the endoplasmic reticulum (reviewed in Zimmermann et al., Biochim Biophys Acta, 1808:912-924, 2011).

In normal cells, quality control systems prevent the accumulation of toxic misfolded protein species. However, in response to mutagenesis, aging or oxidative stress, misfolding can often occur escaping quality control (Soskic et al., Exp. Gerontol., 43: 247-257, 2008; Zeng et al., Mech. Ageing Dev., 126: 760-766, 2005; Shpund & Gershon, Arch. Gerontol. Geriatr., 24: 125-131, 1997).

As postmitotic cells, neurons appear to be particularly sensitive to these effects and many neurodegenerative disorders, such as Alzheimer's, Parkinson's, and Huntington's diseases, involve aberrant accumulation of misfolded or misprocessed proteins. Genetic studies have routinely linked Hsp70 and its co-chaperones to this process, and thus, it has emerged as a potential drug target (Evans et al., J Med Chem., 53:4585-4602, 2010). Alzheimer's disease (AD) is the most common neurodegenerative disease, and its patients are characterized by progressive memory loss and the accumulation of senile plaques (SP) composed of β-amyloid (Aβ) and neurofibrillary tangles (NFTs) assembled from tau. Current models suggest that self-association of Aβ or tau into β-sheet rich oligomers leads to neuronal cell death. Hsp70 has been shown to play important roles in the cytotoxicity of both Aβ and tau (for review see (Evans et al., J Med Chem., 53:4585-4602, 2010). For example, Hsp72 blocks the early stages of Aβ aggregation in vitro at substoichiometric levels (Evans et al., J Biol Chem., 281:33182-33191, 2006), and Hsp70 has been shown to alter processing of the amyloid precursor protein (Kumar et al., Hum Mol Genet., 16:848-864, 2007). Also, this chaperone protects against Aβ-induced cytotoxicity via inhibiting caspase-9 and accelerating the elimination of Aβ (Veereshwarayya et al., J Biol Chem., 281:29468-29478, 2006). In addition to these effects on Aβ, Hsc70 also binds tau at two sites within its tubulin-binding repeats, which is the same region required for tau self-association (Sarkar et al., J Neurosci Res., 86(12):2763-2773, 2008). This finding suggests that Hsc70 might compete with aggregation and toxicity and, consistent with this model, overexpression of Hsp70 reduces aggregated tau in mouse models (Petrucelli et al., Hum Mol Genet., 13:703-714, 2004).

Pharmacological Upregulation of Hsp70 Expression

Many pharmacological agents have been demonstrated to increase cellular expression of Hsp70 through various mechanisms (Sloan et al., Curr Opin Drug Discov Devel., 12:666-681, 2009). A distinction should, however, be made between molecules that act by a defined stimulation within the Hsp70 regulatory pathway and those that affect Hsp70 levels by introducing a cellular stress. Compounds that use the latter stress-inducing mechanism may have a higher propensity to cause cell death or other unwanted effects as a result of chronic stressing, and thus may be less desirable as therapeutic agents. A further distinction of the modes of action of different Hsp70 upregulators can be made between Hsp70 inducers, which increase Hsp70 expression under a broad range of stress conditions, and Hsp70 co-inducers, which act solely to potentiate a pre-existing stress response and have little or no effect in non-stressed or healthy systems. The co-inducer mechanism may therefore selectively exhibit an effect in diseased tissue, thereby inherently reducing the risk of unwanted side effects in healthy tissue (Sloan et al., Curr Opin Drug Discov Devel., 12:666-681, 2009).

Modulators of Protein Processing

Proteasome inhibitors such as bortezomib (Lauricella et al., Apoptosis, 11:607-625, 2006), MG-132 and lactacystin (Kim et al., Biochem Biophys Res Commun., 264:352-358, 1999) demonstrate significant HSF-1-mediated Hsp70 induction via inhibition of protein degradation, accumulation of unfolded protein and induction of the cellular stress response (Sloan et al., Curr Opin Drug Discov Devel., 12:666-681, 2009). Lactacystin selectively induces the heat shock response (HSR) in preference to the unfolded protein response, and reduces nuclear inclusions in a neuronal P127Q Huntington's disease model (Kim et al., J Neurochem., 91:1044-1056, 2004). In many cases, Hsp70 induction is accompanied by other, mechanism-based and undesirable cellular effects or apoptosis (Sloan et al., Curr Opin Drug Discov Devel., 12:666-681, 2009). Although proteasome inhibitors are approved for clinical use in oncology, their limited therapeutic window may preclude significant applicability of these drugs in the treatment of protein-folding diseases.

Chemically Reactive Inducers

Chemical induction of Hsp70 has been described about N-ethylmaleimide (Senisterra et al., Biochemistry, 36:11002-11011, 1997), electrophilic serine protease inhibitors such as 3,4-dichloroisocoumarin (DCIC) and N-a-tosyl-L-lysine chloromethyl ketone (TLCK) (Rossi et al., J Biol Chem., 273:16446-16452, 1998), curcumin, a major constituent of turmeric (Dunsmore et al., Crit Care Med., 29:2199-2204, 2001), cyclopentenone PGs, characterized by PGA1, Δ7-PGA1, PGA2 and Δ12-PGJ2 (Lee et al., Proc Natl Acad Sci USA, 92:7207-7211, 1995).

The cyclopentenone PGs—are able to induce Hsp70 and are reported to induce HSF-1 activation (7- to 15-fold) (Hamel et al., Cell Stress Chaperones, 5:121-131, 2000). Sodium salicylate enhances Hsp70 induction in spinal cord cultures (1 mM/40° C.) compared with heat shock alone, and indomethacin reduces the temperature required for HSF-1 activation in HeLa cells under heat shock conditions at a dose of 250 µM. This activity of indomethacin correlates with an increase in HSF-1 phosphorylation and a cytoprotective effect in HeLa cells; pretreatment with indomethacin (250 µM/40° C.) improved cellular survival rate of a subsequent 44.5° C. heat shock from 3% with no pretreatment to approximately 40% (Lee et al., Proc Natl Acad Sci USA, 92:7207-7211, 1995).

Recent evidence has also suggested that PPARγ agonists may have utility other than their well-characterized insulin sensitizing effects in Hsp-dependent processes: the reduction of Hsp70 inducibility observed in the heart of an insulin-resistant rat model was ameliorated by treatment (10 mg/kg/day) with the PPARγ agonist pioglitazone. Additional reperfusion experiments also demonstrated that pioglitazone assisted functional recovery in isolated rat hearts (Taniguchi et al., Diabetes, 55: 2371-2378, 2006).

Celastrol, a quinine methide triterpene isolated from preparations used in Chinese herbal medicine, potently co-induces Hsp70 in concert with other stresses via an HSF-1-dependent mechanism (Westerheide et al., J Biol Chem., 279:56053-56060, 2004). This drug has demonstrated neuroprotection in Huntington's models of polyQ aggregation (Zhang et al., J Mol Med., 85:1421-1428, 2007), and cytoprotection in mouse transgenic models of amyotrophic lateral sclerosis (Kiaei et al., Neurodegener Dis., 2:246-254, 2005). Several other natural products including the triterpenoid enones glycyrrhizin (Yan et al., Cell Stress Chaperones, 9:378-389, 2004) and carbenoxolone (Nagayama et al., Life Sci., 69:2867-2873, 2001), as well as the masked acetal paeoniflorin (Yan et al., Cell Stress Chaperones, 9:378-389, 2004), may induce Hsp70 by similar mechanisms to celastrol.

Co-Inducing Hydroxylamine Derivatives

A family of hydroxylamine derivatives, including the prototype bimoclomol, were identified as co-inducers of the HSR with utility in a range of disease models-(Vigh et al., Nat Med., 3:1150-1154, 1997). Treatment of myogenic rat H9c2 cells with bimoclomol (10 µM) 16 h prior to heat shock resulted in a 4-fold increase in Hsp70 levels relative to heat shock alone (Vigh et al., Nat Med., 3:1150-1154, 1997), with this induction providing cytoprotection (at 100 µM) in rat neonatal cardiomyocytes undergoing a lethal heat shock (Polakowski et al., Eur J Pharmacol., 435:73-77, 2002). The mechanism of action is thought to be via binding and modulation of phosphorylation of HSF-1 leading to effects on HSF-1/DNA binding (Hargitai et al., Biochem Biophys Res Commun., 307:689-695, 2003), although additional effects related to stabilization of membranes during heat shock have been noted (Torok et al., Proc Natl Acad Sci USA, 100:3131-3136, 2003).

The bimoclomol analog BRX-220 has been demonstrated to significantly elevate Hsp70 level relative to vehicle in neurons following trauma (Kalmar et al., Exp Neurol., 176:87-97, 2002). The free base of BRX-220, arimoclomol, also delayed the progression of an amyotrophic lateral sclerosis phenotype in a mouse model (Kalmar et al., J Neurochem., 107:339-350, 2008; Kieran et al., Nat Med., 10:402-405, 2004).

Another hydroxylamine derivative NG-094 significantly ameliorated polyQ-mediated animal paralysis in C. elegans model, reduced the number of Q35-YFP aggregates and delayed polyQ-dependent acceleration of aging (Haldimann et al., J Biol Chem., 286:18784-18794, 2011).

Metabolites and Nutrients

Relatively high doses of several metabolites and nutrients have also exhibited effects on Hsp levels, with associated functional benefits: α-lipoic acid ameliorated Hsp70 deficiency in patients with Type 1 diabetes (Strokov et al., Bull Exp Biol Med., 130:986-990, 2000); and studies in brains of aged rats demonstrated increased Hsp expression (Hsp70 and heme oxygenase) in response to dosing with acetyl-1-carnitine, a compound that is found in mitochondrial membranes (Calabrese et al., Antioxid Redox Signal, 8:404-416, 2006).

Teprenone utilized in gastric ulcer treatment is a well-characterized inducer of Hsp70 that has exhibited cytoprotective benefit in several models including gastric necrosis (Tomisato et al., Biol Pharm Bull., 24:887-891, 2001), cerebral infarction (Nagai et al., Neurosci Lett., 374:183-188, 2005), hepatotoxicity (Nishida et al., Toxicology, 219 (1-3):187-196, 2006) and inflammation (Mochida et al., J Clin Biochem Nutr., 41:115-123, 2007). Other chaperones, including HspB8 (Sanbe et al., PLoS ONE, 4:e5351, 2009), are also induced by teprenone, which may further contribute to the cytoprotective properties of the molecule. Carvacrol, a major compound in oil of many *Origanum* species, had a capacity to co-induce cellular Hsp70 expression in vitro (Wieten et al., Arthritis Rheum., 62:1026-1035, 2010). Carvacrol specifically promoted T cell recognition of endogenous Hsp70 as was shown in vitro by the activation of an Hsp70-specific T cell hybridoma and amplified T cell responses to Hsp70 in vivo (Wieten et al., Arthritis Rheum., 62:1026-1035, 2010).

Miscellaneous Hsp70 Inducers

The SirT-1 activator resveratrol induces Hsp70 and exhibits cytoprotection in response to heat shock and hydrogen peroxide treatment in human peripheral lymphocytes (Putics et al., Antioxid Redox Signal, 10:65-75, 2008).

Riluzole, an FDA approved drug for the treatment of amyotrophic lateral sclerosis, demonstrated a co-induction of Hsp70 in a reporter gene assay with heat shock. This effect, which was ablated in HSF-1 knockout cells, was thought to be caused by a stabilization of the cytosolic HSF-1 pool (Yang et al., PLoS ONE, 3:e2864, 2008).

Elesclomol has demonstrated efficacy in Phase II clinical trials for the treatment of metastatic melanoma by increasing the quantity of reactive oxygen species (ROS) in cells and selectively inducing apoptosis in hypoxic tumour cells. This effect was accompanied by a tumour cell-specific increase in hypoxic tumour cells (Revill et al., Elesclomol. Drugs Future (2008) 33:310-315), however, development of this drug was recently suspended because of safety concerns.

Other compounds that act to induce Hsp70 through sometimes incompletely characterized mechanisms include ectoine, a natural product isolated from halophilic microorganisms (Buommino et al., Cell Stress Chaperones, 10:197-203, 2005), diazoxide (O'Sullivan et al., J Neurotrauma, 24:532-546, 2007), and imidazothiadiazole (Salehi et al., Chem Biol., 13(2):213-223, 2006).

Many of the Hsp70 inducers described above may rely on the covalent modification of proteins for their mode of action, and could lead to initiation of the HSR, which may be problematic because of non-specific effects and immunogenicity. In some cases, molecules may simply be cell stressors, activating the cellular defence mechanisms including Hsp expression. This chronic stressing of cells may deliver short-term efficacy, but the long-term effects on cellular response and viability are less easily predicted Co-inducer compounds that potentiate the response to a pre-existing stress without exhibiting effects in non-stressed environments may provide a higher degree of tissue selectivity compared with non-specific stressors by acting to potentiate pre-existing but inadequate stress responses to ongoing disease-related stress.

Genetic Upregulation of Hsp70

The augmentation of Hsp70 has demonstrated beneficial effects in several overexpression studies, and in many cases has been associated with cytoprotection or attenuation of stress-induced injury (Broome et al., FASEB J., 20:1549-1551, 2006; Choo-Kang et al., Am J Physiol Lung Cell Mol Physiol., 281:L58-68, 2001; Chung et al., Proc Natl Acad Sci USA, 105(5):1739-1744, 2008; Marber et al., J Clin Invest., 95:1446-1456, 1995; Muchowski et al., Proc Natl Acad Sci USA, 97:7841-7846, 2000; Zheng et al., J Cereb Blood Flow Metab., 28:53-63, 2008). The exposure of cells or whole organisms to temperatures in excess of 40° C. ('heat stressing') causes the upregulation of chaperones, including Hsp70. Many different compensatory mechanisms are activated during heat stressing, and therefore, it is difficult to assess which effects are caused solely by Hsp70. In order to overcome this challenge, mice that overexpress solely the rat Hsp70 on promotion with β-actin have been developed. In these transgenic mice the overexpression of the rat inducible 70-kD heat stress protein increases the resistance of the heart to ischemic injury (Marber et al., J Clin Invest., 95:1446-1456, 1995). In another study, Hsp72 overexpressing mice exhibited resistance to diet-induced hyperglycemia (Chung et al., Proc Natl Acad Sci USA, 105:1739-1744, 2008), and a reduction in age-related markers of oxidative stress (lipid peroxidation, glutathione content, superoxide dismutase and catalase levels) (Broome et al., FASEB J., 20:1549-1551, 2006). An increased expression (~10-fold) of specific isoforms of Hsp70 has also been demonstrated in Hsp70 overexpressing mice, and was accompanied by a reduced susceptibility to brain ischemia/reperfusion injury (Zheng et al., J Cereb Blood Flow Metab., 28:53-63, 2008). This protection from brain ischemia was accompanied by a reduction in the activation of NFκB throughout the brain as a whole, suggesting that Hsp70 may ameliorate ischemic injury by reducing inflammatory processes (Zheng et al., J Cereb Blood Flow Metab., 28:53-63, 2008). The effect of the overexpression of Hsp70 on discrete protein-folding processes has been demonstrated in an in vitro model of Huntington's disease, the aggregation of the huntingtin protein bearing extended polyglutamine repeats was significantly reduced in yeast that overexpressed Hsp70 (or Hsp40), suggesting a direct role for these chaperones in preventing the misfolding and/or aggregation of this pathogenic protein (Muchowski et al., Proc Natl Acad Sci USA, 97:7841-7846, 2000).

Similarly, in a cell model of cystic fibrosis, trafficking of the cystic fibrosis transmembrane conductance regulator (CFTR) containing the misfolding-prone ΔF508 mutant could be normalized in IB-3 cells with plasmid-induced overexpression of Hsp70, implying that Hsp70 has a role in chaperoning and correctly folding the mutant CFTR, enabling it to be trafficked to the cell surface (Choo-Kang et al., Am J Physiol Lung Cell Mol Physiol., 281:L58-68, 2001).

Small Hsps

Unlike the ATPase chaperones Hsp100, Hsp90, Hsp70, and Hsp60, the small Hsps (sHsps) with a conserved α-crystalline domain that passively binds misfolded intermediates, independently from ATP hydrolysis (Jakob et al., J Biol Chem., 268:1517-1520, 1993). Without stress, sHsps are mostly assembled into large oligomeric complexes (Garrido et al., Cell Cycle, 5:2592-2601, 2006), which, under stress conditions, may dissociate into amphiphilic dimers that prevent misfolding polypeptides from aggregating (Jakob et al., J Biol Chem., 268:1517-1520, 1993) and protect membranes from heat disruption (Haslbeck et al., Nat Struct Mol Biol., 12:842-846, 2005; Horvath et al., Biochimica et Biophysica Acta (BBA)—Biomembranes, 1778:1653-1664, 2008). sHsps cooperate with Hsp70/Hsp40 and Hsp100 or the GroEL/GroES chaperone networks in refolding of misfolded proteins (for a review, see (Nakamoto et al., Cell Mol Life Sci., 64:294-306, 2007). Human Hsp27 and Hsp70 are often, although not obligatorily, co-expressed in response to a variety of physiological and environmental stimuli (Garrido et al., Cell Cycle, 5:2592-2601, 2006; Vigh et al., Trends Biochem Sci., 32:357-363, 2007). As sHsps have strong cytoprotective properties (Garrido et al., Cell Cycle, 5:2592-2601, 2006), their inhibition is an important target in pharmacological therapies to cancer (Didelot et al., Curr Med Chem., 14:2839-2847, 2007), whereas the upregulation sHsps may prevent liver damage (Kanemura et al., J Gastrointest Surg., 13:66-73, 2009) or pathologies caused by protein misfolding, such as Alzheimer's (Fonte et al., J Biol Chem 283:784-791, 2008; Wu et al., Neurobiol Aging, 31:1055-1058, 2010), Parkinson's (Zourlidou et al., J Neurochem., 88:1439-1448, 2004), and Huntington's disease (Perrin et al., Mol Ther., 15(5):903-911, 2007). According to a recent study Hsp27 can protect neurons against the acute and chronic toxic effects of ethanol in transgenic mouse model (Toth et al., Cell Stress and Chaperones, 15:807-817, 2010).

Although Hsp modulating small compounds are known and some of them are under clinical trials none of them has been marketed as pharmaceutically active agent so far. There remains an increasing need for specific potent Hsp modulating compounds to meet the demanding biological and pharmaceutical requirements to proceed towards human clinical trials. The ideal candidates for therapeutic use would be compounds which do not induce/silence the classical heat-shock protein response per se. Instead, they only modulate the expression of specific classes of lisps altered by mild physical or pathophysiological stresses. Such Hsp co-modulators are unique drug candidates because they may enhance/decrease HSP expression in diseased cells, without significantly affecting healthy cells thereby less likely that they have major side effects.

Thus, principal aim of the present invention is the provision of compounds with selective stress protein modulating activity, especially co-modulating activity, whereby they are useful in the treatment of neurodegenerative disorders, cancer diseases, metabolic syndromes, lysosomal storage diseases skin diseases and additionally could be used in combinational therapies.

The present invention provides certain partly novel 1,4-dihydropyridines with selective Hsp modulating activity. It has been surprisingly and unexpectedly found that said compounds show selective Hsp co-modulating activity, which has not been described for 1,4-dihydropyridine derivatives so far.

A huge number of documents disclosed 1,4-dihydropyridine derivatives and their uses but none of them disclosed the use of the specific compounds of the present invention as Hsp modulators.

1,4-Dihydropyridines are particularly well known in pharmacology as L-type calcium channel blockers (Edraki et al., Drug Discovery Today, 14:1058-1066, 2009); and have been extensively used in the treatment of cardiovascular diseases (Hope & Lazzara, Adv Intern Med., 27:435-52, 1982). Calcium antagonist 1,4-dihydropyridines have been described for use in the treatment of neuropathies in diabetes (Taber, J. et al., U.S. Pat. No. 5,438,144). The derivatives of 4-(3-chlorophenyl)-5-substituted-carbamoyl-1,4-dihydropyridine-3-carboxylic acid showed selective inhibitory action of N-type calcium channel, and were effective in the treatment of acute stage of ischemic cerebrovascular disorders; progressive neurodegenerative diseases such as Alzheimer's disease, AIDS related dementia, Parkinson's disease etc. (Nakajo, A. et al., U.S. Pat. No. 6,610,717). Some ester derivatives of 4-nitrophenyl-1,4-dihydropyridine-5-phosphonic acid are useful for treating cancer or a pre-cancerous condition (Krouse, A. J., WO 2008/137107). Compounds with condensed 1,4-dihydropyridine skeleton have been reported to reduce elevated blood glucose level (Ono, M. et al., WO 2005/025507) or to prevent cancerous cells to divide (Mauger, J., et al., WO 2007/012972). 2,6-Unsubstituted-1,4-dihyropyridine derivatives possesses sirtuin deacetylase activity and may be used for the treatment of cancer, metabolic, cardiovascular, and neurodegenerative diseases (Antonello et al., J. Med. Chem., 52:5496-504, 2009). N-substituted-1,4-dihydropyridines have been reported to have coronary vasodilator and antihypertensive activity (Meyer, H. et al., HU 164867). Some N-substituted-1,4-dihydropyridine derivatives are useful in the treatment of acute and chronic ischaemic disorders by improving blood viscosity (Behner, O., EP 0 451 654), while other N-substituted derivatives showed selective $Ca^{2+}$ dependent $K^+$ channel modulating activity and were useful for the treatment of CNS disorders (Heine, H., G., EP 0 705 819 and Heine, H., G., EP 0 717 036).

SUMMARY OF THE INVENTION

The invention is directed towards partly new 1,4-dihydropyridine derivatives which show broad utility by exhibiting Hsp modulating activity and thereby are useful in the treatment and prevention of diseases and pathophysiological conditions mediated by Hsps.

The present invention is based on the unexpected finding that the 1,4-dihydropyridine derivatives of formula (I)—while having no or negligible effect on Ca-channels—are capable of selectively co-modulating Hsp activity which means that they act solely by potentiating or inhibiting a pre-existing stress response and have little or no effect in non-stressed or healthy systems, they exhibit effect selectively in diseased tissue, and thereby they may reduce the risk of unwanted side effects in healthy tissue. The 1,4-dihydropyridine derivatives of formula (I), which are co-modulators may provide suitable therapeutic drug candidates for many disease states. Depending on the specific Hsp class involved the 1,4-dihydropyridine derivatives of formula (I) are useful according to a non-limiting embodiment in the treatment and prevention of neurodegenerative diseases, cancer diseases, metabolic syndromes, lysosomal storage disorders or skin disorders. As defined earlier, a stress protein co-modulator is a substance that does not affect Hsp production by itself, but can modulate Hsp induction in combination with other mild stresses which are present under different disease states. Since the compounds of invention are capable of modulating the stress response in stressed cells while not affecting unstressed cells, they are unlikely to produce major side effects in contrast with many classes of current drugs.

DETAILED DESCRIPTION OF THE INVENTION

In one aspect the present invention provides 1,4-dihydropyridine derivatives of formula (I)

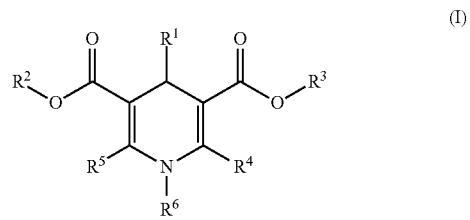

wherein
$R^1$ is $C_{6-24}$aryl group optionally substituted with one or more substituents independently selected from the group consisting of halogen, straight-chained or branched $C_{1-6}$alkyl, halo$C_{1-6}$alkyl, $C_{1-6}$alkoxy, 5 to 6 membered heteroaryl comprising 1 to 4 nitrogen atoms, —CN, —SO$_2$NH$_2$, $C_{2-6}$alkenyl, $C_{2-6}$alkynyl, $C_{3-8}$cycloalkyl and alk-X-alk group wherein X is O, S, SO, $SO_2$ and alk is $C_{1-6}$alkyl; or 5 to 6 membered heteroaryl group comprising 1 to 3 nitrogen atoms or other heteroatoms like oxygen and sulphur, and combinations thereof;

$R^2$ and $R^3$ are independently hydrogen or $C_{1-6}$alkyl group;

$R^4$ and $R^5$ are independently hydrogen, $C_{1-6}$alkyl group optionally substituted with amino, mono- or di($C_{1-6}$ alkyl) amino, or with 5 to 24 membered optionally fused heterocyclic ring attached by nitrogen and optionally comprising additional 1 to 3 N, O, S heteroatoms and optionally substituted with $C_{1-6}$alkyl group or $C_{1-6}$alkoxy group;

$R^6$ is $C_{1-6}$ alkyl, $C_{3-7}$cycloalkyl, $C_{3-7}$cycloalkyl$C_{1-6}$alkyl or aryl$C_{1-6}$alkyl group;

and stereoisomers including enantiomers, diastereomers, racemic mixtures, mixture of enantiomers and combination thereof, as well as polymorphs, pharmaceutically acceptable salts, solvates, esters and prodrugs thereof for use in the therapeutic or prophylactic treatment of a disorder mediated by a heat shock protein.

Further aspects of the invention provide compounds of formula (I) as described above for use in the therapeutic or prophylactic treatment of a disorder mediated by Hsp70 and Hsp25, and wherein the Hsp mediated disorder is selected from the group consisting of neurodegenerative diseases, cancer diseases, metabolic syndromes, lysosomal storage diseases and skin disorders conditions, and wherein the treatment further comprises administering at least one therapeutic agent selected from the group consisting of agents useful for the treatment of neurodegenerative diseases, cancer diseases, metabolic syndromes, lysosomal storage diseases or skin disorders.

Another aspect of the invention provides a pharmaceutical and optionally cosmetical composition comprising a compound of formula (I) as described above and one or more pharmaceutically acceptable or cosmetically acceptable carriers and/or excipients for use in the therapeutic or prophylactic treatment of a disorder mediated by a Hsp.

Further aspects of the invention provide a pharmaceutical and optionally cosmetical composition comprising a compound of formula (I) as described above and one or more pharmaceutically acceptable or cosmetically acceptable carriers and/or excipients for use in the therapeutic or prophylactic treatment of a disorder mediated by a Hsp, wherein the disorders are selected from the group consisting of neurodegenerative diseases, cancer diseases, metabolic syndromes, lysosomal storage diseases and skin disorders conditions, and wherein the treatment further comprises administering at least one therapeutic agent selected from the group consisting of agents useful for the treatment of neurodegenerative diseases, cancer diseases, metabolic syndromes, lysosomal storage diseases or skin disorders.

Another aspect of the invention provides a compound of formula (I) as described above for use in combination therapy wherein the combination therapy comprises administering an effective amount of a compound of formula (I) as described above to a patient simultaneously, separately or sequentially with a thermal treatment or with other therapies used for the treatment of the given pathophysiological state.

Another aspect of the invention provides certain new compounds of formula (I) as described below and stereoisomers including enantiomers, diastereomers, racemic mixtures, mixture of enantiomers and combination thereof, as well as polymorphs, pharmaceutically acceptable salts, solvates, esters and prodrugs thereof in enantiomerically enriched form, furthermore pharmacological and cosmetical compositions comprising the same as well.

Abbreviations

Figure 1:
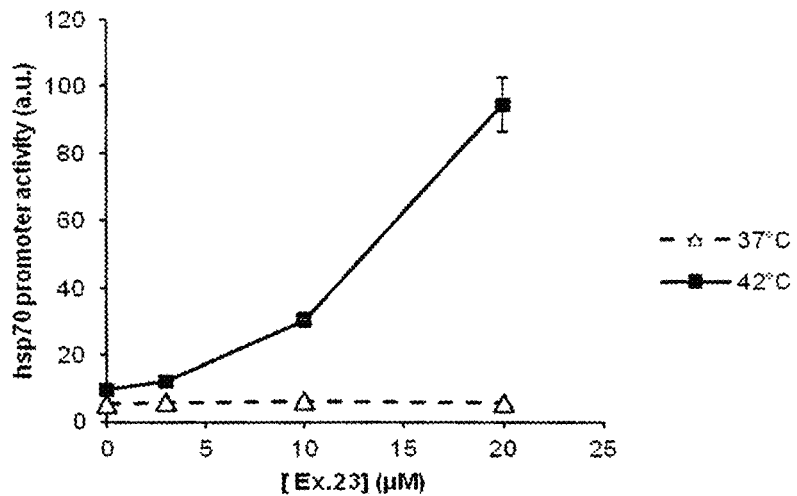
FIG. 1 Hsp70 co-inducing activity of compound of Ex. 23 on SHSY5Y cells

Aβ β-amyloid
AD Alzheimer's Disease
APP Amyloid Precursor Protein
ATPase Adenosine Triphosphatase
CFTR Cystic Fibrosis Transmembrane Conductance Regulator
DCIC 3,4-Dichloroisocoumarin
DMEM-F12 Dulbecco's Modified Eagle Medium: Nutrient Mixture F-12
GFP Green Fluorescent Protein
HSF Heat Shock Factor
Hsp Heat Shock Protein
HSR Heat Shock Response
MTD Maximum Tolerated Dose
NEF Nucleotide Exchange Factors
NFκB Nuclear Factor kappa-Light-Chain-Enhancer of Activated B Cells
NFTs Neurofibrillary Tangles
PB Physiological Saline
PBS Phosphate Buffered Saline
PGS Prostaglandin
PPARγ Peroxisome Proliferator-activated Receptor γ
PVDF Polyvinylidene Difluoride
SDS-PAGE Sodium Dodecyl Sulfate-Polyacrylamide Gel Electrophoresis
SP Senile Plaques
TLCK N-a-Tosyl-L-Lysine Chloromethyl Ketone
YFP Yellow Fluorescent Protein Definitions The term "Hsp modulating" refers to a process, which either increases or decreases cellular expression, membrane association and/or function of Hsp100, Hsp90, Hsp70, Hsp60, and the "small Hsp" proteins through various mechanisms.

The term "HSP co-modulating activity" refers to the action of "HSP co-modulators", which do not modulate stress response by themselves but are able to modify it in the presence of mild stress or pathophysiological conditions. Chaperone co-modulators act like "smart drugs" by selective interactions with only those cells, which are under acute or chronic stress. These types of molecules may provide an important novel therapy in a number of acute and chronic diseases which either increase or decrease cellular expression, membrane association and/or function of Hsp100, Hsp90, Hsp70, Hsp60, and the "small Hsp" proteins through various mechanisms.

Furthermore "modulation" refers also to changing the ratio of different Hsps.

The term "Hsp upregulation" refers to a process, which increases cellular expression and/or functioning of Hsp100, Hsp90, Hsp70, Hsp60, and the "small Hsp" proteins through various mechanisms.

The term "Hsp inducer" refers to compounds, which increase Hsp expression under a broad range of pathophysiological conditions unlike to Hsp co-inducers, which act solely to potentiate a pre-existing stress response and have little or no effect in non-stressed or healthy systems.

The terms Hsp "chaperone co-inducer" or Hsp "co-inducer" refer to compounds, which do not induce stress response by themselves but are able to modify it in the presence of mild stress or pathophysiological conditions. Chaperone co-inducers act like "smart drugs" by selective interactions with only those cells, which are under acute stress. These types of molecules may provide an important novel therapy in a number of acute and chronic diseases.

The term "Hsp silencer" refers to a compound, which decrease Hsp expression and/or functioning under a broad range of stress including pathophysiological conditions.

The term "Hsp inhibitor" refers to a compound, which is capable of demonstrating detectable inhibition of one or more Hsps. Inhibition of Hsps may be determined using the methods described and incorporated by reference herein (Wyshocka et al., Mol. Cel. Biochem. 215:153-156, 2000).

The skilled person realizes that an in vivo Hsp inhibitor is not necessarily an in vitro Hsp inhibitor, for example a prodrug form of a compound demonstrates little or no activity in in vitro assays. Such prodrug forms may be altered by metabolic or other biochemical processes in the patient to provide an in vivo active compound.

The term "prodrug" refers to any pharmaceutically acceptable salt, ester or other derivative of a compound of the invention, which upon administration to a recipient is capable of providing either directly or indirectly a compound of the invention or a pharmaceutically active metabolite or residue thereof. Various forms of prodrugs are well known in the art. See for example Design of Prodrugs, Bundgaard, A. Ed., Elseview, 1985 and Method in Enzymology, Widder, K. et al, Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference.

The term "pathophysiological conditions" refers to any disease, disorder or effect that produces deleterious biological consequences in a subject.

The pathophysiological conditions which are selectively modulated by heat shock protein activity of the compounds of invention include, but are not limited to for example neurodegenerative diseases, which are characterized by progressive nervous system dysfunction, in particular, Alzheimer disease, frontotemporal dementia, dementia with Lewy bodies, corticobasal degeneration, progressive supranuclear palsy, prion disorders, multiple system atrophy, amyotrophic lateral sclerosis (ALS or Lou Gehrig's Disease), Parkinson's disease, Huntington's disease, poly-Q related neurodegenerative diseases, multiple sclerosis, hereditary spastic paraparesis, spinocerebellar atrophies, brain cancer related diseases, degenerative nerve diseases, encephalitis, epilepsy, genetic brain disorders, head and brain malformations, hydrocephalus, stroke related diseases, prion diseases, amyloidoses, Friedreich's ataxia, metabolic (diabetes) related diseases, toxin related diseases, Charcot-Marie-Tooth neuropathy and others;

cancer diseases, particularly breast cancer, small-cell lung cancer, melanoma, squamous cell carcinoma, non-small-cell lung cancer, bladder cancer, head and neck cancer, ovarian cancer, prostate cancer, Kaposi's sarcoma, glioblastoma, glioma, colorectal cancer, genitourinary cancer, gastrointestinal cancer, renal cancer, hematological cancers, cervical cancer, colon cancer, cutaneous t-cell lymphoma, esophageal cancer, liver cancer, neuroblastoma, oral dysplasia, pancreatic cancer, peripheral t-cell lymphoma pheochromocytoma, sarcoma, testicular cancer, thyroid cancer and the like;

non-Hodgkin's lymphoma, lymphoma, multiple myeloma, leukemia (including acute myelogenous leukemia, chronic myelogenous leukemia, chronic lymphocytic leukemia), myelodysplastic syndrome and mesothelioma;

metabolic syndromes and related disorders caused by or manifested as increased insulin resistance, impaired glucose tolerance, Type 2 diabetes mellitus, central obesity, elevated level of triglycerides, decreased HDL cholesterol, prothrombotic and pro-inflammatory states, polycystic ovarian syndrome (PCOS) and the like;

lysosomal storage diseases, particularly (aspartylglucosaminuria, cystinosis, Fabry disease, Farber disease, fucosidosis, galactosialidosis, Gaucher disease, GM1 gangliosidoses, Morquio B, GM2 gangliosidoses (O, B, AB, B1 variants), Krabbe disease, metachromatic leukodystrophy (arylsulfatase A and SAP1 deficient), mucolipidoses II and III (Icell disease), mucolipidosis I (Sialidosis), mucolipidosis IV, mucopolysaccharidosis I (Hurler and Scheie syndromes), mucopolysaccharidosis II (Hunter syndrome), mucopolysaccharidosis III (Sanfilippo syndrome A, B, C, D), mucopolysaccharidosis IV (Morquio syndrome A, B), mucopolysaccharidosis VI (MaroteauxLamy syndrome), mucopolysaccharidosis VII (βglucuronidase deficiency), multiple sulfatase deficiency, neuronal ceroid lipofuscinosis, Niemann-Pick disease (A, B, and C), Pompe disease, pycnodysostosis, Schindler disease, sialic acid storage disease, Wolman disease (cholesterol ester storage disease), α-mannosidosis, β-mannosidosis;

skin disorders, particularly non-infectious rashes (dermatitis, psoriasis, and others), UVinduced inflammations, non-cancerous skin growths (seborrheic keratoses, keratoacanthomas, keloids and others), and skin cancer (basal cell carcinoma, squamous cell carcinoma, melanoma, Kaposi's sarcoma, Paget's disease of the nipple).

The term "thermal therapy" also called "hyperthermia therapy" refers to medical treatment in which body tissue is either exposed to slightly higher temperatures or body temperature is increased by the induction of fever to treat diseases and conditions, particularly cancer, inflammation, metabolic syndrome, benign prostatic hyperthropy, to reduce hemorrhoids, to stimulate the immune system, to increase the level of disease fighting white blood cells, to treat pain.

The term "metabolic syndrome" refers to a combination of medical conditions that, when occurring together, increase the risk of developing cardiovascular disease and diabetes. Symptoms and features include fasting hyperglycemia (Type 2 diabetes mellitus, impaired glucose tolerance, or increased insulin resistance); high blood pressure; central obesity; overweight with fat deposits; decreased HDL cholesterol; elevated triglycerides.

The term "subject" refers to animal, or to one or more cells derived from an animal. Preferably, the animal is a mammal, most preferably a human. Cells may be in any form, including but not limited to cells retained in tissue, cell clusters, immortalized cells, transfected or transformed cells, and cells derived from an animal that have been physically or phenotypically altered.

The term "patient" refers to any mammal, preferably humans.

A "pharmaceutically acceptable salt" may be prepared from any compound of the invention having functionality capable of forming salts, for example a base or acid functionality. Pharmaceutically acceptable salts may be prepared with organic or inorganic acids or bases. Compounds of the invention that contain one or more basic functional groups, (e.g., amino, alkylamino), are capable of forming pharmaceutically acceptable salts with pharmaceutically acceptable organic and inorganic acids. These salts can be prepared in situ during the final isolation and purification of the compounds of the invention, or by separately reacting a purified compound of the invention in its free base form with a suitable organic or inorganic acid, and isolating the salt thus formed. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-napthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Compounds of the present invention that contain one or more acidic functional groups are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the pure compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative pharmaceutically acceptable cations include alkali or alkaline earth salts such as lithium, sodium, potassium, calcium, magnesium, and aluminum salts and the like. Illustrative examples of some of the bases that can be used include sodium hydroxide, potassium hydroxide, choline hydroxide, sodium carbonate, tetrabutylammonium hydroxid, and the like. Representative organic amines useful for the formation of base addition salts include ethylamine, diethylamine, ethylenediamine, ethanolamine, diethanolamine, piperazine and the like. This invention also envisions the quaternization of any basic nitrogen-containing groups of the compounds disclosed herein. Water or oil-soluble or dispersible products may be obtained by such quaternization. See, for example, Berge et al. "Pharmaceutical Salts", J. Pharm. Sci. 1977, 66:1-19.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "alkyl" as used herein refers to an optionally substituted straight-chain, or optionally substituted branched chain saturated hydrocarbon radical having from one to six carbons. Examples of alkyl radicals include methyl, ethyl, n-propyl, isopropyl, n-butyl, isobutyl, sec-butyl, tert-butyl, tert-amyl, pentyl, hexyl and the like.

The term "cycloalkyl" as used herein refers to cyclic alkyl monoradicals wherein each cyclic moiety has from three to seven carbon atoms. Examples of cycloalkyl radicals include cyclopropyl, cyclobutyl, cyclopentyl, cyclohexyl and the like.

The term "alkoxy" as used herein refers to an alkyl-O— group wherein the term alkyl is defined as above. Examples of alkoxy groups include methoxy, ethoxy, n-propoxy, iso-propoxy, n-butoxy, iso-butoxy, sec-butoxy, tert-butoxy and the like.

The term "aryl" as used herein refers to an aryl group having six to ten skeletal ring carbons, for example phenyl and naphthyl.

The term "arylalkyl" as used herein refers to an alkyl radical as defined above in which at least one H atom is replaced by an aryl radical as defined above, for example benzyl, 2-phenylethyl and the like.

The term "heteroaryl" as used herein refers to aromatic groups containing five to six skeletal ring atoms where one to four of the ring atoms is a nitrogen atom or a heteroaryl group comprising 1 to 3 nitrogen atoms or other heteroatoms like oxygen and sulphur, and combinations thereof. Examples of heteroaryl include, without limitation furanyl, thiophenyl, pyridyl, pyrrolyl, pyrimidyl, pyrazinyl, imidazolyl, pyrazolyl, triazolyl, tetrazolyl, thiazolyl, oxazolyl, and the like.

The term "alk-X-alk" as used herein refers to alk-O-alk, alk-S-alk, alk-SO-alk, alk-SO$_2$-alk groups wherein alk is an alkyl group containing one to six carbon atoms. Examples of alk-X-alk include without limitation methoxymethyl, ethoxymethyl, methylthiomethyl, ethylthiomethyl, methylsufinylmethyl, ethylsulfinylmethyl, methylsulfonylmethy, ethylsulfonylmethyl, and the like.

The term "halogen" as used herein refers to fluoro, chloro, bromo, iodo.

The term "heterocyclic" as used herein refers to optionally substituted and fused, and in heterocyclic part partially saturated ring radicals containing from five to twenty four ring atoms where one of the ring atoms is nitrogen and optionally the additional heteroatoms are such as for example oxygen, nitrogen, sulphur for example without limitation pirrolidinyl, piperidyl, piperazinyl, pyrrolidinyl, morpholinyl, tetrahydroisoquinolinyl, tetrahydrobenzazepinyl and the like. The said heterocyclic rings may be optionally substituted in any position with alkyl, alkoxy radicals as defined above.

The term "mono- or dialkylamino" as used herein refers to the groups —NHR, —NRR' where R and R' are alkyl as defined above.

"Optionally substituted" groups may be substituted or not substituted.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

Further, it is possible using well known techniques to separate the various forms, and some embodiments of the invention may feature purified or enriched species of a given enantiomer or diastereomer.

A "pharmacological or dermatological or cosmetical composition" refers to a mixture of one or more of the compounds described herein, or pharmaceutically acceptable salts thereof, with other chemical components, such as pharmaceutically and/or dermatologically or cosmetically acceptable carriers and/or excipients. The purpose of a pharmacological composition is to facilitate administration of a compound to an organism.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include without limitation: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

An "excipient" refers to an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

A "pharmaceutically effective amount" means an amount which is capable of providing a therapeutic and/or prophylactic effect. The specific dose of compound administered according to this invention to obtain therapeutic and/or prophylactic effect will, of course, be determined by the particular circumstances surrounding the case, including, for example, the specific compound administered, the route of administration, the pathophysiological conditions being treated, and the individual being treated. A typical daily dose (administered in single or divided doses) will contain a dosage level of from about 0.01 mg/kg to about 50-100 mg/kg of body weight of an active compound of the invention. Preferred daily doses generally will be from about 0.05 mg/kg to about 20 mg/kg and ideally from about 0.1 mg/kg to about 10 mg/kg. Factors such as clearance rate, half-life and maximum tolerated dose (MTD) have yet to be determined but one of ordinary skill in the art can determine these using standard procedures.

Pharmaceutical compositions comprising a compound of formula (I) as active component may additionally comprise an agent useful for the treatment of neurodegenerative diseases, cancer diseases, metabolic syndromes, lysosomal storage diseases or skin disorders, or the pharmaceutical compositions comprising a compound of formula (I) may be co-administered with such agents.

The additional agent useful for the treatment of neurodegenerative diseases, cancer diseases, metabolic syndromes, lysosomal storage diseases or skin disorders means, but not limited to antitumor agents, to agents for oral antidiabetic medications, for anti-dementia medications, for anti-Parkinson medications, for anti-multiple sclerosis medications, for anti-ALS medications, for anti-Friedreich's ataxia medications, for anti-antiepilepsy medications, and others.

Antitumour agents include, but are not limited to for example alkylating agents (cyclophosphamide, ifosfamide, carmustine, and the like), anti-metabolites (methotrexate, raltitrexed, pemetrexed, cytarabine, fludarabine, cytarabine, fluorouracil, tegafur, gemcitabine, capecitabine, and the like), plant alkaloids and terpenoids (vinblastine, vincristine, vindesine, vinorelbine, paclitaxel, docetaxel and the like), topoisomerase inhibitors (etoposide, irinotecan, topotecan, amsacrine, etoposide phosphate, teniposide and the like, cytotoxic antibiotics (actinomycin, doxorubicin, daunorubicin, valrubicin, idarubicin, epirubicin, bleomycin, plicamycin, mitomycin and the like), and other antitumour agents (cisplatin, carboplatin, oxaliplatin, and the like)

Agents for oral anti-diabetic medications include, but are not limited to for example insulin and analogues, biguanides (metformin, buformin and the like), thiazolidinediones (rosiglitazone, pioglitazone and the like), sulfonylureas (tolbutamide, acetohexamide, tolazamide, chlorpropamide, glipizide, glyburide, glimepiride, gliclazide, and the like), nonsulfonylurea secretagogues (repaglinidine, nateglinidine and the like), alpha-glucosidase inhibitors (miglitol, acarbose and the like), incretin mimetics (exenatide, liraglutide, taspoglutide, and then like), dipeptidyl peptidase-4 (DPP-4) inhibitors (vildagliptin, sitagliptin, saxagliptin, linagliptin and the like), amylin analogues (pramlintide and the like).

Agents for anti-dementia medications include, but are not limited to for example donepezil, galantamine, rivastigmine, memantime and the like. Antiparkinson medications include, but are not limited to for example biperiden, metixene, procyclidine, L-DOPA, amantadine, ropinirole, pramipexole, selegiline, entacapone, and the like. Anti-ALS drug (riluzole). Anti-multiple sclerosis medications include, but are not limited to for example fingolimod, interferon-beta-1a and 1b, glatiramer acetate, mitoxantrone, natalizumab and the like. Anti-Friedreich's ataxia medications (idebenone). Anti-antiepilepsy medications include, but are not limited to for example carbamazepine, clorazepate, clonazepam, ethosuximide, felbamate, fosphenytoin, gabapentin, lacosamide, lamotrigine, levetiracetam, oxcarbazepine, phenobarbital, phenytoin, pregabalin, primidone, tiagabine, topiramate, valproate semisodium, valproic acid, zonisamide, clobazam, vigabatrin and the like.

Agents for treatment of lysosomal storage diseases include, but are not limited to for example glycosyltransferase inhibitors, β-glucocerebrosidase, imigluderase; agalsidase alpha, agalsidase beta, aglucosidase alpha, laronidase, idursulphase, galsulphase, α-glucosidase, N-butyldeoxynojirimycin, 1-deoxynojirimycin, galactose, galactostatin bisulphite, isofagomine, 2,5-anhydro-2,5-D-glucitol, N-octyl-4-epi-b-valienamine, pyrimethamine and the like.

The pharmaceutical compositions of this invention may be administered orally, parenterally, by inhalation spray, topically, rectally, nasally, buccally, vaginally or via an implanted reservoir.

The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

Topical administration of the pharmaceutical or dermatological compositions of this invention is especially useful when the desired treatment involves areas or organs readily accessible by topical application. For application topically to the skin, the pharmaceutical or dermatological composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

These compositions can be prepared by methods known per se in the preparation of pharmaceutical compositions and cosmetics, by mixing the active material and the corresponding carriers and/or excipients. The compositions generally contain 0.5 to 99.5% by weight active compound.

Compounds of the Invention

The present invention provides partly novel 1,4-dihydropyridine derivatives of formula (I)

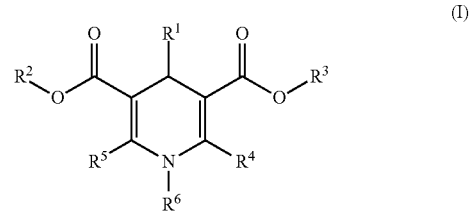

(I)

wherein $R^1$ is $C_{6-24}$aryl group optionally substituted with one or more substituents independently selected from the group consisting of halogen, —$NO_2$, straight-chained or branched $C_{1-6}$alkyl, halo$C_{1-6}$alkyl, $C_{1-6}$alkoxy, 5 to 6 membered heteroaryl comprising 1 to 4 nitrogen atoms, —CN, —$SO_2NH_2$, $C_{2-6}$alkenyl, $C_{2-6}$alkynyl, $C_{3-8}$cycloalkyl and alk-X-alk group wherein X is O, S, SO, $SO_2$ and alk is $C_{1-6}$alkyl; or 5 to 6 membered heteroaryl group comprising 1 to 3 nitrogen atoms or other heteroatoms like oxygen and sulphur, and combinations thereof;

$R^2$ and $R^3$ are independently hydrogen or $C_{1-6}$alkyl group;

$R^4$ and $R^5$ are independently hydrogen, —CN, $C_{1-6}$alkyl group optionally substituted with amino, mono- or di($C_{1-6}$ alkyl)amino, or with 5 to 24 membered optionally fused heterocyclic ring attached by nitrogen and optionally comprising additional 1 to 3 N, O, S heteroatoms and optionally substituted with $C_{1-6}$alkyl group or $C_{1-6}$alkoxy;

$R^6$ is $C_{1-6}$ alkyl, $C_{3-7}$cycloalkyl, $C_{3-7}$cycloalkyl$C_{1-6}$alkyl or aryl$C_{1-6}$alkyl group; and stereoisomers including enantiomers, diastereomers, racemic mixtures, mixture of enantiomers and combination thereof, where appropriate, as well as polymorphs, pharmaceutically acceptable salts, solvates, esters and prodrugs thereof for use in the therapeutic or prophylactic treatment of a disorder mediated by a heat shock protein.

In some embodiments $R^1$ is a phenyl group independently optionally substituted with one or two halogen, halo$C_{1-6}$alkyl; $R^2$, $R^3$ are independently $C_{1-6}$alkyl group; $R^4$, $R^5$ are independently $C_{1-6}$alkyl group optionally substituted with amino, mono- or di($C_{1-6}$ alkyl)amino, or with 5 to 24 membered optionally fused heterocyclic ring attached by nitrogen and optionally comprising additional 1 to 3 N, O, S heteroatoms and optionally substituted with $C_{1-6}$alkyl group or $C_{1-6}$alkoxy group; $R^6$ is $C_{1-6}$alkyl.

In a preferred embodiment $R^1$ is a phenyl group substituted with halo$C_{1-6}$alkyl; $R^2$, $R^3$ are independently $C_{1-6}$alkyl group; $R^4$, $R^5$ are independently $C_{1-6}$alkyl group optionally substituted with mono- or di($C_{1-6}$ alkyl)amino, or with 5 to 24 membered optionally fused heterocyclic ring attached by nitrogen and optionally comprising additional 1 to 3 N, O, S heteroatoms and optionally substituted with $C_{1-6}$alkyl group or $C_{1-6}$alkoxy group; $R^6$ is $C_{1-6}$alkyl.

In an alternative preferred embodiment $R^1$ is a phenyl group substituted with halo$C_{1-6}$alkyl; $R^2$, $R^3$ are independently $C_{1-6}$alkyl group; $R^4$, $R^5$ are independently $C_{1-6}$alkyl group optionally substituted with mono- or di($C_{1-6}$ alkyl)amino, or with 6 membered heterocyclic ring attached by nitrogen and optionally comprising additional N heteroatom and optionally substituted with $C_{1-6}$alkyl group; $R^6$ is $C_{1-6}$alkyl.

In other selected preferred embodiment $R^1$ is a phenyl group substituted with fluoro-$C_{1-6}$alkyl; $R^2$ and $R^3$ are $C_{1-6}$alkyl group; $R^4$ and $R^5$ are independently $C_{1-6}$alkyl group optionally substituted with di($C_{1-6}$alkyl)amino, or with 5 to 12 membered optionally fused heterocyclic ring attached by nitrogen and optionally comprising one additional N heteroatom and optionally substituted with $C_{1-6}$alkyl or $C_{1-6}$alkoxy group; $R^6$ is $C_{1-6}$alkyl.

TABLE 1

Exemplary compounds of formula (I)

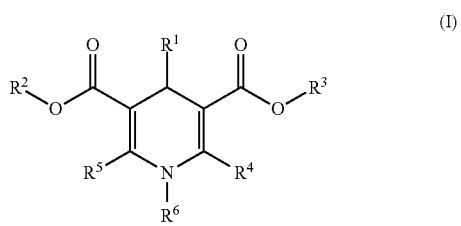

(I)

| No. | $R^1$ | $R^2$ | $R^3$ | $R^4$ | $R^5$ | $R^6$ |
|---|---|---|---|---|---|---|
| 1 | 4-$F_3$C—Ph | Me | Me | Me | Me | Me |
| 2 | 4-F—Ph | Me | Me | Me | Me | Me |
| 3 | Ph | Me | Me | Me | Me | Me |
| 4 | 4-Cl—Ph | Me | Me | Me | Me | Me |
| 5 | 4-Me—Ph | Me | Me | Me | Me | Me |
| 6 | 4-MeO—Ph | Me | Me | Me | Me | Me |
| 7 | 3-$F_3$C—Ph | Me | Me | Me | Me | Me |
| 8 | 2-$F_3$C—Ph | Me | Me | Me | Me | Me |
| 9 | 3-$NO_2$—Ph | Me | Me | Me | CN | Me |
| 10 | 4-(1-imidazolyl)-Ph | Me | Me | Me | Me | Me |
| 11 | 4-$F_3$C—Ph | Me | Me | Me | Me | Et |
| 12 | 4-(3-pyridyl)-Ph | Me | Me | Me | Me | Me |
| 13* | 4-$F_3$C—Ph | Me | Me | Me | 2-(1-pyrrolidinyl)-Et | Me |
| 14 | 4-$F_3$C—Ph | Me | Me | Me | 2-($Me_2$N)—Et | Me |
| 15* | 4-$F_3$C—Ph | Me | Me | Me | 2-(1-morpholinyl)-Et | Me |
| 16* | 4-$F_3$C—Ph | Me | Me | 2-(4-methyl-1-piperidinyl)-Et | 2-(4-methyl-1-piperidinyl)-Et | Me |
| 17* | 4-$F_3$C—Ph | Me | Me | 2-(1-piperidinyl)-Et | 2-(1-piperidinyl)-Et | Me |
| 18 | 2-Cl—Ph | Me | Me | Me | Me | Me |
| 19* | 2-Cl—Ph | Me | Me | 2-(1-pyrrolidinyl)-Et | 2-(1-pyrrolidinyl)-Et | Me |
| 20* | 2-Cl—Ph | Me | Me | Me | 2-(1-morpholinyl)-Et | Me |
| 21* | 2-Cl—Ph | Me | Me | 2-(4-methyl-1-piperidinyl)-Et | 2-(4-methyl-1-piperidinyl)-Et | Me |
| 22* | 2-Cl—Ph | Me | Me | 2-($Me_2$N)—Et | 2-($Me_2$N)—Et | Me |
| 23* | 4-$F_3$C—Ph | Me | Me | 2-($Me_2$N)—Et | 2-($Me_2$N)—Et | Me |
| 24 | 3,5-diF—Ph | Me | Me | Me | Me | Me |
| 25* | 3,5-diF—Ph | Me | Me | Me | 2-($Me_2$N)—Et | Me |
| 26* | 3,5-diF—Ph | Me | Me | Me | 2-($Me_2$N)—Et | Me |
| 27 | 4-$F_3$C—Ph | Me | Me | Et | Et | Me |
| 28 | 4-$F_3$C—Ph | Me | i-Pr | Me | Me | Me |
| 29 | 4-$F_3$C—Ph | Me | i-Bu | Me | Me | Me |
| 30* | 4-$F_3$C—Ph | Me | Me | 2-($Me_2$N)—Et | 2-(1-piperidinyl)-Et | Me |
| 31* | 4-$F_3$C—Ph | Me | Me | 2-($Me_2$N)—Et | 2-(1-morpholinyl)-Et | Me |
| 32 | 4-$F_3$C—Ph | Me | Et | Me | Me | Me |
| 33 | 4-$F_3$C—Ph | Et | Et | H | H | c-Pr |
| 34 | 4-$F_3$C—Ph | Et | Et | H | H | Bz |
| 35 | 4-$F_3$C—Ph | H | Me | Me | Me | Me |
| 36 | 4-$F_3$C—Ph | H | H | Me | Me | Me |
| 37 | 4-$F_3$C—Ph | Et | Et | H | H | Me |
| 38 ref. Ex | Ph | Et | Et | H | H | Bz |
| 39 ref. Ex. | Ph | H | H | H | H | Bz |
| 40** | 4-$F_3$C—Ph | Me | Me | 2-(1,2,3,4-tetrahydroisoquinolin-2-yl)-Et | Me | Me |
| 41* | 4-$F_3$C—Ph | Me | Me | 2-(6,7-dimethoxy-1,2,3,4-tetrahydroisoquinolin-2-yl)-Et | Me | Me |
| 42* | 4-$F_3$C—Ph | Me | Me | 2-(6,7-dimethoxy-1,2,3,4-tetrahydroisoquinolin-2-yl)-Et | 2-($Me_2$N)—Et | Me |
| 43** | 4-$F_3$C—Ph | Me | Me | 2-(1,2,4,5-tetrahydro-bezo[d]azepin-3-yl)-Et | Me | Me |
| 44 | furan-2-yl | Me | Me | Me | Me | Me |
| 45 | thiophen-3-yl | Me | Me | Me | Me | Me |
| 46* | 4-$F_3$C—Ph | Me | Me | (pyrrolidin-1-yl)-Me | Me | Me |
| 47 | 4-$F_3$C—Ph | Me | Me | CN | Me | Me |
| 48* | 4-$F_3$C—Ph | Me | Me | (piperidin-1-yl)-Me | Me | Me |
| 49* | 4-$F_3$C—Ph | Me | Me | (1,2,3,4-tetrahydroisoquinolin-2-yl)-Me | Me | Me |

*HCl salt
**fumarate salt

Selected compounds of this invention include, but are not limited to Examples 1, 4, 5, 6, 7, 8, 11, 12, 14, 15, 16, 17, 23, 24, 25, 26, 27, 33, 34, 35, 41, 42, 43, 44, 45, 47, 49.

EXAMPLES

The following examples are only for the purposes of illustration of the invention and are not intended to limit the spirit or the scope of the claims.

Preparation of the Compounds of the Invention

The compounds of formula (I) may be synthesized using conventional techniques [Hantzsch, A., "Condensationprodukte aus Aldehydammoniak and Ketonartigen Verbindungen", *Chemische Berichte* 14 (2): 1637-1638 (1881), Jing-Jing Xia, Guan-Wu Wang "One-Pot Synthesis and Aromatization of 1,4-Dihydropyridines in Refluxing Water", *Synthesis* 2005 (14): 2379-2383 (2005)]. For example compounds of the invention may be prepared using the processes described herein. As can be appreciated by the skilled practitioner, these processes are not the only means by which the compounds described and claimed may be synthesized. Further methods will be evident to those of ordinary skill in the art.

Advantageously, these compounds are conveniently synthesized from commercially available starting materials. Otherwise their preparation is referenced or described herein.

Compounds of the invention are characterized by HNMR data (recorded in deuteriated solvents on a 400 MHz Bruker spectrometer) and/or melting points.

General Procedures

Procedure A

A mixture of 0.05 mol of aldehyde, 0.1 mol of methyl acetoacetate (or the corresponding ketoester), 0.05 mol methylamine-hydrochloride (or other alkylamine salt) was refluxed in 25 ml pyridine for 5 hours. After evaporation of the solvent the residue was dissolved in dichloromethane, washed with water. The organic phase was dried and evaporated. The residue was crystallized from methanol Procedure B 1 mmol of dihydropyridine, 2 mmol of dimethylamine-hydrochloride (or other amine), 2 mmol of paraformaldehyde and 1 ml acetic acid were mixed and heated on 95° C. for 1 hour. The mixture was evaporated, dissolved in water and extracted with ether. After separation the aqueous phase was neutralised and extracted with ethyl acetate. The organic phase was dried and evaporated and the residue was purified by column chromatography on $Al_2O_3$ with s mixture of hexane/ethyl acetate. The pure fractions were collected, transferred to hydrochloride salts and recrystallized from methanol-diethyl ether.

Procedure C 1 mmol of dihydropyridine, 5 mmol of dimethylamine-hydrochloride (or other amine), 5 mmol of paraformaldehyde and 1 ml acetic acid were mixed and heated on 95° C. for 5 hours. The mixture was evaporated, dissolved in water and extracted with ether. After separation the aqueous phase was neutralised with $NaHCO_3$ and extracted with ethyl acetate. The organic phase was dried and evaporated and the residue was purified by column chromatography on silica with s mixture of hexane/ethyl acetate. The pure fractions were collected, transferred to hydrochloride or to other salts and recrystallized from methanol diethyl ether.

Procedure D 5 mmol of aldehyde, 5 mmol of methyl 3-aminocrotonate and 5 mmol of isopropyl(ethyl or tert-butyl) acetoacetate were dissolved in methanol and refluxed for 16 hours. After evaporation the residue was dissolved in 20 ml mol of tetrahydrofurane and a suspension of 2 equivalent in NaH in 10 ml THF was carefully added and stirred at room temperature for 3 hours. Then 2 equivalent of methyl iodide was added. After 2 hours the product was carefully decomposed with methanol. The product was dissolved in water and extracted with ethyl acetate. The organic phase was dried and evaporated. The organic phase was dried and evaporated and the residue was purified by column chromatography on silica with s mixture of hexane/ethyl acetate. The pure fractions were collected, and recrystallized from hexane.

Procedure E

A mixture of 1 mmol dihydropyridine, 5N KOH (5 ekv.) and 10 ml ethanol was stirred at 80° C.—on for 8 hours. After evaporation the residue was dissolved in 25 ml water and acidified with 2N of HCl. The crystalline product was filtered off and was purified by column chromatography on $Al_2O_3$ with s mixture of toluene/methanol. The pure fractions were collected recrystallized from diisopropyl ether-methanol.

Procedure F

A mixture of 1 mmol dihydropyridine, 5N KOH (10 ekv.) and 10 ml ethanol was stirred at 80° C.—on for 2 days. After evaporation the residue was dissolved in 25 ml water and acidified with 2N of HCl. The crystalline product was filtered off, washed with water and recrystallized from a mixture of methanol and acetonitrile.

Procedure G 1 mmol of Dimethyl 2-(2-dimethylaminoethyl)-1,6-dimethyl-4-(4-trifluoromethylphenyl)-1,4-dihydropyridine-3,5-dicarboxylate hydrochloride (or a corresponding dihydropyridine derivative), 5 mmol of the corresponding secondary amine 5 mmol of paraformaldehyde and 1 ml acetic acid were mixed and heated on 95° C. for 1 hour. The mixture was evaporated, dissolved in water and extracted with ether. After separation the aqueous phase was neutralised and extracted with ethyl acetate. The organic phase was dried and evaporated and the residue was purified by column chromatography on $Al_2O_3$ with s mixture of hexane/ethyl acetate. The pure fractions were collected, transferred to hydrochloride salts and recrystallized from methanol diethyl ether.

Procedure H 6 mmol of ethyl propiolate, 3 mmol of aldehyde and 3 mmol of the corresponding amine were dissolved in 0.2 ml acetic acid. The mixture was heated at 80° C. for 3 hours. After cooling it was mixed with water and extracted with ethyl acetate, dried and evaporated. The residue was crystallized from n-hexane.

Procedure I

The corresponding 2-methyl dihydropyridine derivative was transformed to 2-bromomethyl derivative in pyridine with pyridiniumbromoperbromide ((ref. *Chem. Pharm. Bull.* 45, 1997, 869). 1 mmol of this product was solved in 10 ml acetonitrile and 2 eq. of $K_2CO_3$ and 1.2 eq. of the corresponding amine was added. The mixture was stirred till the reaction was completed, filtered and evaporated and the residue was chromatographed.

Procedure J

The corresponding 2-methyl dihydropyridine derivative was transformed to 2-formyl derivative in DMSO in the presence of $NaHCO_3$ ((ref. *Chem. Pharm. Bull.* 45, 1997, 869). 1 mmol of this product was solved in acetic acid and one eq. of hydroxylamine HCl and 1.5 eq of NaOAc was added. After one hour stirring 4 mmol of acetic anhydride was added and the mixture was refluxed for 3 hours. After evaporation the residue was neutralized and the 2-cyano derivative was extracted with ethyl acetate, and purified after drying and evaporation by column chromatography.

TABLE 2

Physical data of compounds of formula (I)

| Structure | Ex. No. | Chemical Name | Mp. (° C.) | General Method |
|---|---|---|---|---|
| 4-CF₃-C₆H₄ derivative | 1 | Dimethyl 1,2,6-trimethyl-4-(4-trifluoromethylphenyl)-1,4-dihydropyridine-3,5-dicarboxylate | 159-160 | A |
| 4-F-C₆H₄ derivative | 2 | Dimethyl 1,2,6-trimethyl-4-(4-fluorophenyl)-1,4-dihydropyridine-3,5-dicarboxylate | 184-185 | A |
| C₆H₅ derivative | 3 | Dimethyl 1,2,6-trimethyl-4-phenyl-1,4-dihydropyridine-3,5-dicarboxylate | 201-203 | A |
| 4-Cl-C₆H₄ derivative | 4 | Dimethyl 1,2,6-trimethyl-4-(4-chlorophenyl)-1,4-dihydropyridine-3,5-dicarboxylate | 179-180 | A |

TABLE 2-continued

Physical data of compounds of formula (I)

| Structure | Ex. No. | Chemical Name | Mp. (° C.) | General Method |
|---|---|---|---|---|
| (structure) | 5 | Dimethyl 1,2,6-trimethyl-4-(4-methylphenyl)-1,4-dihydropyridine-3,5-dicarboxylate | 176-178 | A |
| (structure) | 6 | Dimethyl 1,2,6-trimethyl-4-(4-methoxyphenyl)-1,4-dihydropyridine-3,5-dicarboxylate | 163-164 | A |
| (structure) | 7 | Dimethyl 1,2,6-trimethyl-4-(3-trifluoromethylphenyl)-1,4-dihydropyridine-3,5-dicarboxylate | 118-119 | A |
| (structure) | 8 | Dimethyl 1,2,6-trimethyl-4-(2-trifluoromethylphenyl)-1,4-dihydropyridine-3,5-dicarboxylate | 168-170 | A |
| (structure) | 9 | Dimethyl 2-cyano-1,6-dimethyl-4-(3-nitrophenyl)-1,4-dihydropyridine-3,5-dicarboxylate | 150-151 | J |

TABLE 2-continued

Physical data of compounds of formula (I)

| Structure | Ex. No. | Chemical Name | Mp. (° C.) | General Method |
|---|---|---|---|---|
| 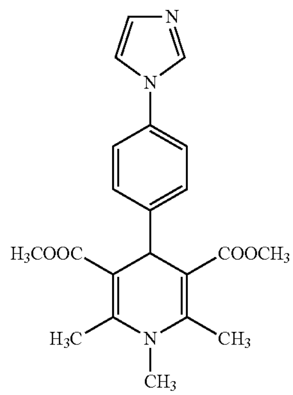 | 10 | Dimethyl 1,2,6-trimethyl-4-(4-(1-imidazolyl)phenyl)-1,4-dihydropyridine-3,5-dicarboxylate | 201-202 | A |
| 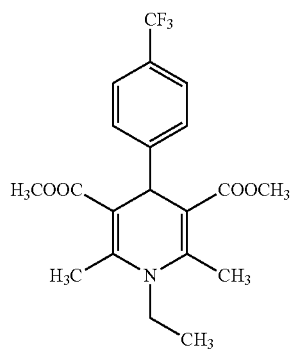 | 11 | Dimethyl 1-ethyl-2,6-dimethyl-4-(4-trifluoromethylphenyl)-1,4-dihydropyridine-3,5-dicarboxylate | 135-137 | A |
| 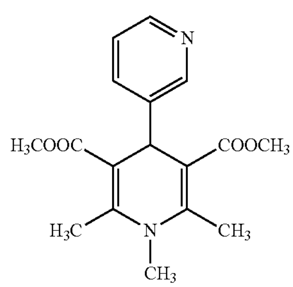 | 12 | Dimethyl 1,2,6-trimethyl-4-(3-piridyl)-1,4-dihydropyridine-3,5-dicarboxylate | 173-175 | A |
| 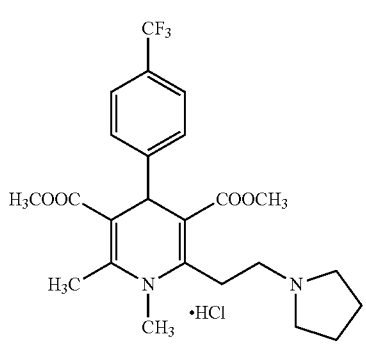 | 13 | Dimethyl 6-(2-pyrrolidin-1-yl-ethyl)-1,2-dimethyl-4-(4-trifluoromethylphenyl)-1,4-dihydropyridine-3,5-dicarboxylate hydrochloride | 218-219 | B |

TABLE 2-continued

Physical data of compounds of formula (I)

| Structure | Ex. No. | Chemical Name | Mp. (° C.) | General Method |
|---|---|---|---|---|
| 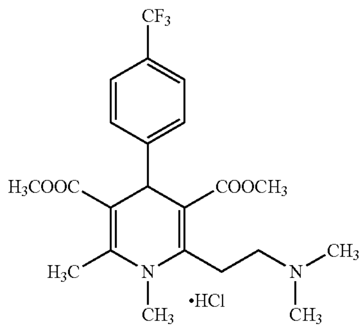 | 14 | Dimethyl 2-(2-dimethylaminoethyl)-1,6-dimethyl-4-(4-trifluoromethylphenyl)-1,4-dihydropyridine-3,5-dicarboxylate hydrochloride | 214-216 | B |
| 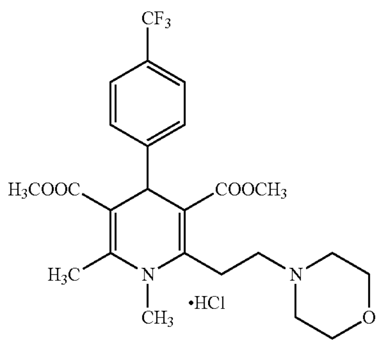 | 15 | Dimethyl 1,2-dimethyl-6-(2-morpholin-4-yl-ethyl)-4-(4-trifluoro-methyl-phenyl)-1,4-dihydropyridine-3,5-dicarboxylate hydrochloride | 188-193 | B |
| 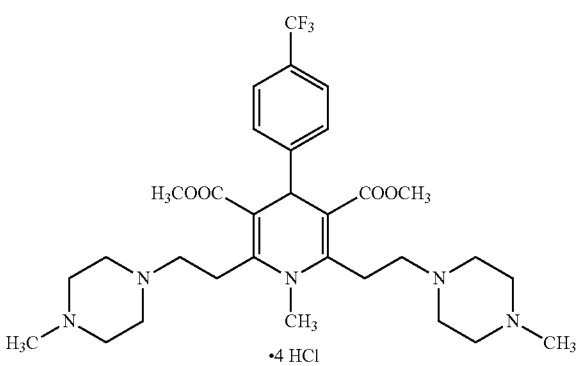 | 16 | Dimethyl 1-methyl-2,6-bis-[2-(4-methyl-piperazin-1-yl)-ethyl]-4-(4-trifluoromethylphenyl)-1,4-dihydropyridine-3,5-dicarboxylate hydrochloride | 195-200 | C |
| 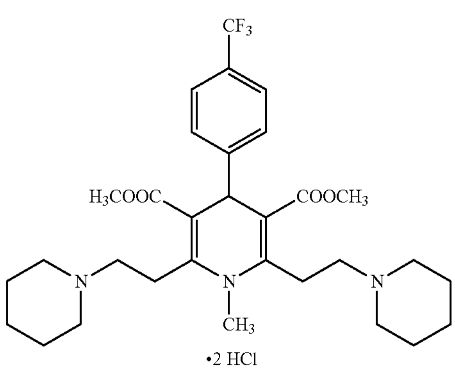 | 17 | Dimethyl 1-methyl-2,6-bis-(2-piperidin-1-yl-ethyl)-4-(4-trifluoromethylphenyl)-1,4-dihydropyridine-3,5-dicarboxylate dihydrochloride | 208-210 | C |

TABLE 2-continued

Physical data of compounds of formula (I)

| Structure | Ex. No. | Chemical Name | Mp. (° C.) | General Method |
|---|---|---|---|---|
| (structure) | 18 | Dimethyl 4-(2-chlorophenyl)-1,2,6-trimethyl-1,4-dihydropyridine-3,5-dicarboxylate | 154-155 | A |
| (structure) | 19 | Dimethyl 4-(2-chlorophenyl)-1-methyl-2,6-bis-(2-pyrrolidin-1-yl-ethyl)-1,4-dihydropyridine-3,5-dicarboxylate dihydrochloride | 188-193 | C |
| (structure) | 20 | Dimethyl 4-(2-chlorophenyl)-1,2-dimethyl-6-(2-morpholin-4-ethyl)-1,4-dihydropyridine-3,5-dicarboxylate hydrochloride | 171-173 | B |
| (structure) | 21 | Dimethyl 4-(2-chlorophenyl)-1-methyl-2,6-bis-[2-(4-methyl-piperazin-1-yl)-ethyl]-1,4-dihydropyridine-3,5-dicarboxylate tetrahydrochloride | 210-215 | C |
| (structure) | 22 | Dimethyl 4-(2-chorophenyl)-2,6-bis-(2-dimethylaminoethyl)-1-methyl-1,4-dihydropyridine-3,5-dicarboxylate dihydrochloride | 241-245 | C |

TABLE 2-continued

Physical data of compounds of formula (I)

| Structure | Ex. No. | Chemical Name | Mp. (° C.) | General Method |
|---|---|---|---|---|
| 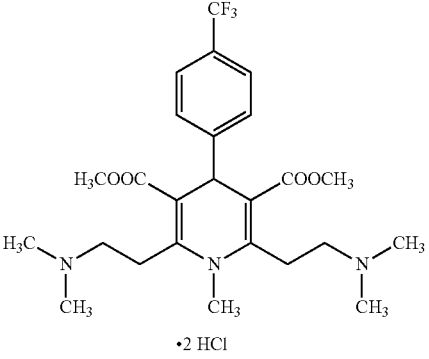 | 23 | Dimethyl 4-(4-trifuoromethylphenyl)-2,6-bis-(2-dimethylaminoethyl)-1-methyl-1,4-dihydropyridine-3,5-dicarboxylate dihydrochloride | 273-276 | C |
| 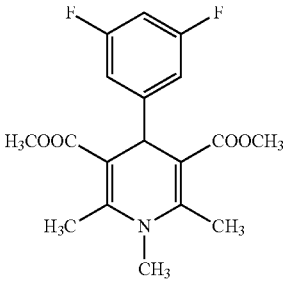 | 24 | Dimethyl 4-(3,5-difluorophenyl)-1,2,6-trimethyl-1,4-dihydropyridine-3,5-dicarboxylate | 167-168 | A |
| 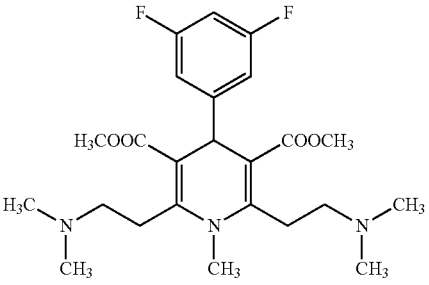 | 25 | Dimethyl 4-(3,5-Difluorophenyl)-2,6-bis-(2-dimethylaminoethyl)-1-methyl-1,4-dihydropyridine-3,5-dicarboxylate dihydrochloride | 261-265 | C |
| 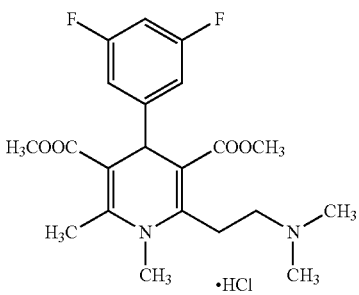 | 26 | Dimethyl 4-(3,5-difluorophenyl)-2-(2-dimethylamino-ethyl)-1,6-dimethyl-1,4-dihydropyridine-3,5-dicarboxylate hydrochloride | 201-203 | B |

TABLE 2-continued

Physical data of compounds of formula (I)

| Structure | Ex. No. | Chemical Name | Mp. (° C.) | General Method |
|---|---|---|---|---|
| (structure) | 27 | Dimethyl 2,6-diethyl-1-methyl-4-(triflouromethyl-phenyl)-1,4-dihydropyridine-3,5-dicarboxylate | 136-138 | A |
| (structure) | 28 | 1,2,6-Trimethyl-4-(4-trifluoromethylphenyl)-1,4-dihydropyridine-3,5-dicarboxylic acid 3-isopropyl ester 5-methyl ester | 92-94 | D |
| (structure) | 29 | 1,2,6-Trimethyl-4-(4-trifluoromethylphenyl)-1,4-dihydropyridine-3,5-dicarboxylic acid 3-tert-butyl ester 5-methyl ester | 128-130 | D |
| (structure) ·2 HCl | 30 | Dimethyl 2-(2-dimethylamino-ethyl)-1-methyl-6-(2-piperidin-1-yl-ethyl)-4-(4-trifluoromethylphenyl)-1,4-dihydropyridine-3,5-dicarboxylate dihydrochloride | 247-249 | E |

TABLE 2-continued

Physical data of compounds of formula (I)

| Structure | Ex. No. | Chemical Name | Mp. (° C.) | General Method |
|---|---|---|---|---|
| (structure with CF$_3$-phenyl, H$_3$COOC, COOCH$_3$, dimethylaminoethyl, morpholinylethyl, N-CH$_3$, ·2 HCl) | 31 | Dimethyl 2-(2-dimethylamino-ethyl)-1-methyl-6-(2-morpholin-1-yl-ethyl)-4-(4-trifluoromethylphenyl)-1,4-dihydropyridine-3,5-dicarboxylate dihydrochloride | 247-248 | E |
| (structure with CF$_3$-phenyl, H$_3$COOC, COOC$_2$H$_5$, H$_3$C, CH$_3$, N-CH$_3$) | 32 | 1,3,6-Trimethyl-4-(4-trifluoromethylphenyl)-1,4-dihydropyridine-3,5-dicarboxylic acid 3-ethyl ester 5-methyl ester | 146-149 | D |
| (structure with CF$_3$-phenyl, C$_2$H$_5$OOC, COOC$_2$H$_5$, N-cyclopropyl) | 33 | Diethyl 1-cyclopropyl-4-(4-trifluoromethylphenyl)-1,4-dihydro-pyridine-3,5-dicarboxylate | 123-124 | H |
| (structure with CF$_3$-phenyl, C$_2$H$_5$OOC, COOC$_2$H$_5$, N-benzyl) | 34 | Dimethyl 1-benzyl-4-(4-trifluoromethylphenyl)-1,4-dihydropyridine-3,5-dicarboxylate | 107-108 | H |

TABLE 2-continued

Physical data of compounds of formula (I)

| Structure | Ex. No. | Chemical Name | Mp. (° C.) | General Method |
|---|---|---|---|---|
| 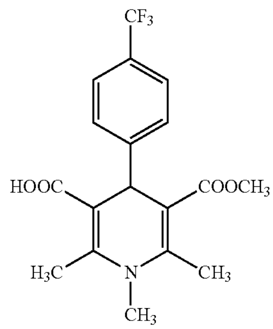 [SMILES: COC(=O)C1=C(C)N(C)C(C)=C(C(=O)O)C1c1ccc(C(F)(F)F)cc1] | 35 | 1,2,6-Trimethyl-4-(4-trifluoromethylphenyl)-1,4-dihydropyridine-3,5-dicarboxylic acid monomethyl ester | 150-155 | E |
| 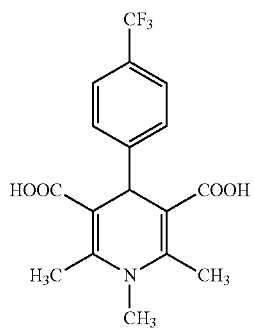 [SMILES: CC1=C(C(=O)O)C(c2ccc(C(F)(F)F)cc2)C(C(=O)O)=C(C)N1C] | 36 | 1,2,6-Trimethyl-4-(4-trifluoromethylphenyl)-1,4-dihydropyridine-3,5-dicarboxylic acid | 152-153 | F |
| 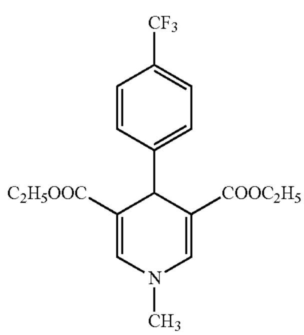 | 37 | Diethyl 1-methyl-4-(4-trifluoromethylphenyl)-1,4-dihydropyridine-3,5-dicarboxylate | 94-96 | H |
| 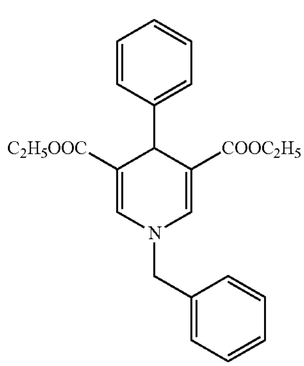 | 38 Ref. Ex. | Diethyl 1-benzyl-4-phenyl-1,4-dihydropyridine-3,5-dicarboxylate | 154-156 | H |

TABLE 2-continued

Physical data of compounds of formula (I)

| Structure | Ex. No. | Chemical Name | Mp. (° C.) | General Method |
|---|---|---|---|---|
| 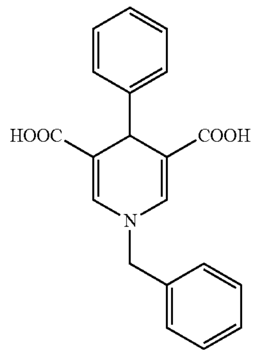 [SMILES: O=C(O)C1=CN(Cc2ccccc2)C=C(C(=O)O)C1c1ccccc1] | 39 Ref. Ex. | 1-Benzyl-4-phenyl-1,4-dihydropyridine-3,5-dicarboxylic acid | 204-206 | F |
| 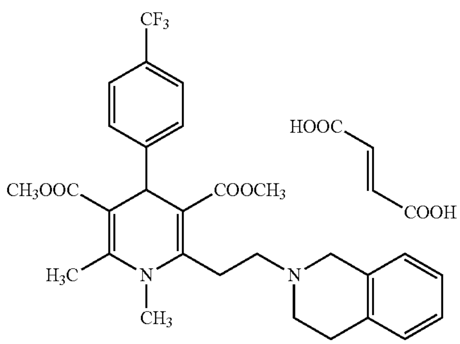 | 40 | Dimethyl 2-[2-(1,2,3,4-tetrahidroisoquinolin-2-yl)-ethyl]-1,6-dimethyl-4-(4-trifluoromethyl-phenyl)-1,4-dihydropyridine-3,5-dicarboxylate fumarate | 186-188 | C |
| 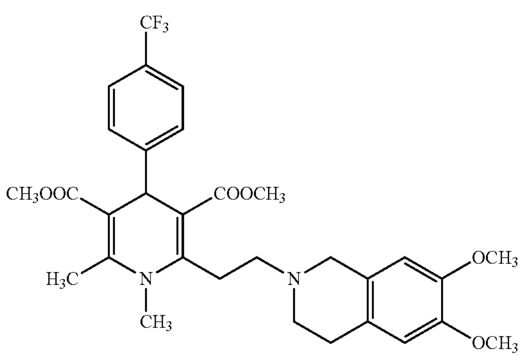 | 41 | Dimethyl 2-[2-(6,7-dimethoxy-1,2,3,4-tetrahydroisoquinolin-2-yl)-ethyl]-1,6-dimethyl-4-(4-trifluoromethylphenyl)-1,4-dihydropyridine-3,5-dicarboxylate hydrochloride | 176-181 | C |
| 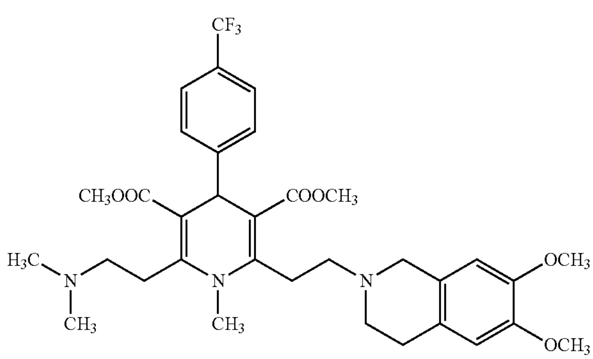 | 42 | Dimethyl 2-[2-(6,7-dimethoxy-1,2,3,4-tetrahydroisoquinolin-2-yl)-ethyl]-6-(2-dimethylamino-ethyl)-1-methyl-4-(4-trifluoromethylphenyl)-1,4-dihydropyridine-3,5-dicarboxylate dihydrochloride | 210-211 | G |

TABLE 2-continued

Physical data of compounds of formula (I)

| Structure | Ex. No. | Chemical Name | Mp. (° C.) | General Method |
|---|---|---|---|---|
| 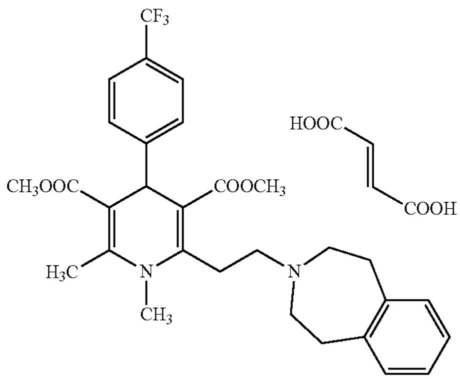 | 43 | Dimethyl 1,2-dimethyl-6-[2-(1,2,4,5-tetrahydro-benzo[d]azepin-3-yl)-ethyl]-4-(4-trifluoromethylphenyl)-1,4-dihydropyridine-3,5-dicarboxylate fumarate | 202-203 | C |
| 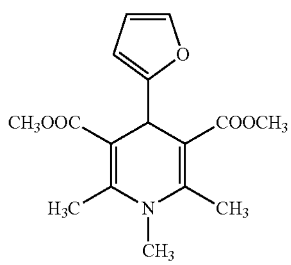 | 44 | Dimethyl 4-(furan-2-yl-1,2,6-trimethyl-1,4-dihydropyridine-3,5-dicarboxylate | 142-143 | A |
| 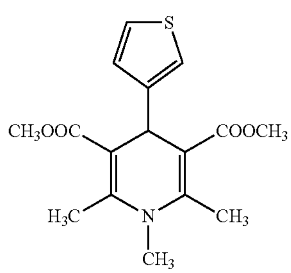 | 45 | Dimethyl 1,2,6-Trimethyl-4-(thiophen-3-yl)-1,4-dihydropyridine-3,5-dicarboxylate | 187-189 | A |
| 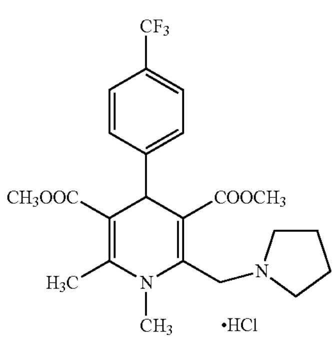 | 46 | Dimethyl 1,2-dimethyl-6-pyrrolidin-1-ylmethyl-4-(4-trifluoromethylphenyl)-1,4-dihydropyridine-3,5-dicarboxylate hydrochloride | 182-185 | I |

TABLE 2-continued

Physical data of compounds of formula (I)

| Structure | Ex. No. | Chemical Name | Mp. (° C.) | General Method |
|---|---|---|---|---|
| 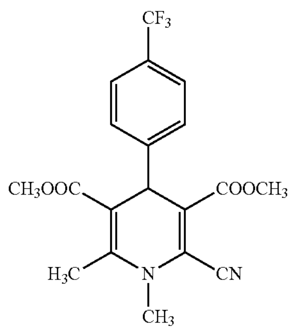 | 47 | Dimethyl 2-cyano-1,6-dimethyl-4-(4-trifluoromethylphenyl)-1,4-dihydropyridine-3,5-dicarboxylate | 129-132 | J |
| 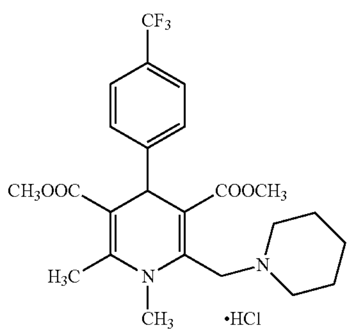 | 48 | Dimethyl 1,2-dimethyl-6-piperidin-1-ylmethyl-4-(4-trifluoromethylphenyl)-1,4-dihydropyridine-3,5-dicarboxylate hydrochloride | 190-192 | I |
| 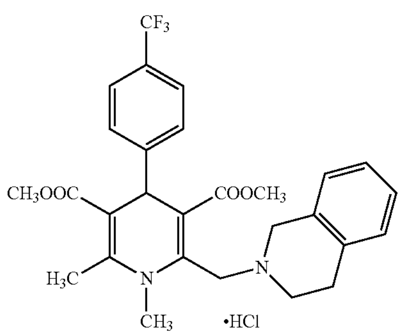 | 49 | Dimethyl 2-(1,2,3,4-tetrahydro-1H-isoquinolin-2-ylmethyl)-1,6-dimethyl-4-(4-trifluoromethylphenyl)-1,4-dihydropyridine-3,5-dicarboxylate hydrochloride | 175-177 | I |
| 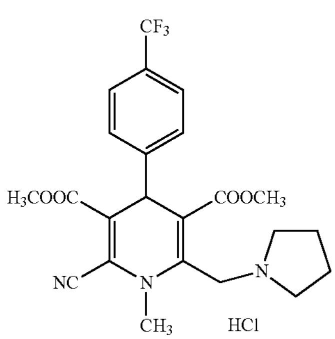 | 50 | Dimethyl 2-cyano-1-methyl-6-pyrrolidin-1-ylmethyl-4-(4-trifluoromethylphenyl)-1,4-dihydropyridine-3,5-dicarboxylate hydrochloride | 173-175 | I |

TABLE 2-continued

Physical data of compounds of formula (I)

| Structure | Ex. No. | Chemical Name | Mp. (° C.) | General Method |
|---|---|---|---|---|
| (structure shown) | 51 | Dimethyl 2-cyano-6-(2-dimethylaminoethyl)-1-methyl-4-(4-trifluoromethylphenyl)-1,4-dihydropyridine-3,5-dicarboxylate hydrochloride | 215-216 | C |

$^1$HNMR data of the compounds synthesized:

Example 1

CDCl$_3$, 400 MHz, δ: 7.45 (d, J=8.0 Hz, 2H, ArH), 7.29 (d, J=8.0 Hz, 2H, ArH), 5.24 (s, 1H, CH), 3.75 (s, 6H, COOCH$_3$), 3.22 (s, 3H, N—CH$_3$), 2.52 (s, 6H, CH$_3$).

Example 2

CDCl$_3$, 400 MHz, δ: 7.06-7.12 (m, 2H, ArH), 6.84-6.91 (m, 2H, ArH), 5.11 (s, 1H, CH), 3.71 (s, 6H, COOCH$_3$), 3.18 (s, 3H, N—CH$_3$), 2.47 (s, 6H, CH$_3$).

Example 3

CDCl$_3$, 400 MHz, δ: 7.17-7.22 (m, 2H, ArH), 7.10-7.15 (m, 3H, ArH), 5.16 (s, 1H, CH), 3.71 (s, 6H, COOCH$_3$), 3.17 (s, 3H, N—CH$_3$), 2.48 (s, 6H, CH$_3$).

Example 4

CDCl$_3$, 400 MHz, δ: 7.13-7.18 (m, 2H, ArH), 7.04-7.09 (m, 2H, ArH), 5.11 (s, 1H, CH), 3.70 (s, 6H, COOCH$_3$), 3.17 (s, 3H, N—CH$_3$), 2.47 (s, 6H, CH$_3$).

Example 5

CDCl$_3$, 400 MHz, δ: 6.97-7.08 (m, 4H, ArH), 5.11 (s, 1H, CH), 3.70 (s, 6H, COOCH$_3$), 3.17 (s, 3H, N—CH$_3$), 2.47 (s, 6H, CH$_3$), 2.27 (s, 3H, Ar—CH$_3$),

Example 6

CDCl$_3$, 400 MHz, δ: 7.06 (d, J=8.8 Hz, 2H, ArH), 6.74 (d, J=8.8 Hz, 2H, ArH), 5.08 (s, 1H, CH), 3.75 (s, 3H, O—CH$_3$), 3.70 (s, 6H, COOCH$_3$), 3.17 (s, 3H, N—CH$_3$), 2.47 (s, 6H, CH$_3$).

Example 7

CDCl$_3$, 400 MHz, δ: 7.31-7.45 (m, 4H, ArH), 5.23 (s, 1H, CH), 3.75 (s, 6H, COOCH$_3$), 3.22 (s, 3H, N—CH$_3$), 2.53 (s, 6H, CH$_3$).

Example 8

CDCl$_3$, 400 MHz, δ: 7.18-7.54 (m, 4H, ArH), 5.53 (s, 1H, CH), 3.64 (s, 6H, COOCH$_3$), 3.26 (s, 3H, N—CH$_3$), 2.32-2.43 (m, 6H, CH$_3$).

Example 10

CDCl$_3$, 400 MHz, δ: 7.79 (s, 1H, ArH), 7.19-7.33 (m, 6H, ArH), 5.19 (s, 1H, CH), 3.73 (s, 6H, COOCH$_3$), 3.21 (s, 3H, N—CH$_3$), 2.50 (s, 6H, CH$_3$).

Example 11

CDCl$_3$, 400 MHz, δ: 7.49 (d, J=8.3 Hz, 2H, ArH), 7.33 (d, J=8.3 Hz, 2H, ArH), 5.20 (s, 1H, CH), 3.75 (s, 6H, COOCH$_3$), 3.73 (t, J=7.0 Hz, 2H, —CH$_2$—CH$_3$), 2.52 (s, 6H, CH$_3$), 1.08 (t, J=7.0 Hz, 3H, —CH$_2$—CH$_3$).

Example 12

CDCl$_3$, 400 MHz, δ: 8.36-8.43 (m, 1H, ArH), 7.43-7.49 (m, 1H, ArH), 7.10-7.17 (m, 1H, ArH), 5.13 (s, 1H, CH), 3.71 (s, 6H, COOCH$_3$), 3.20 (s, 3H, N—CH$_3$), 2.49 (s, 6H, CH$_3$).

Example 13

D$_2$O, 400 MHz, δ: 7.68 (d, J=8.0 Hz, 2H, ArH), 7.45 (d, J=8.0 Hz, 2H, ArH), 5.19 (s, 1H, CH), 3.83 (s, 3H, COOCH$_3$), 3.80 (s, 3H, COOCH$_3$), 3.53-3.58 (m, 8H, —CH$_2$—), 3.34 (s, 3H, N—CH$_3$), 2.51 (s, 3H, CH$_3$), 2.16 (s, 4H, —CH$_2$—).

Example 14

D$_2$O, 400 MHz, δ: 7.62 (d, J=8.6 Hz, 2H, ArH), 7.40 (d, J=8.6 Hz, 2H, ArH), 5.14 (s, 1H, CH), 3.79 (s, 3H, COOCH$_3$), 3.75 (s, 3H, COOCH$_3$), 3.30-3.61 (m, 4H, —CH$_2$—), 3.29 (s, 3H, N—CH$_3$), 2.98 (s, 6H, N(—CH$_3$)$_2$), 2.47 (s, 3H, CH$_3$).

Example 15

D$_2$O, 400 MHz, δ: 7.69 (d, J=8.6 Hz, 2H, ArH), 7.44 (d, J=8.6 Hz, 2H, ArH), 5.24 (s, 1H, CH), 3.87-4.30 (m, 8H, —CH$_2$—), 3.84 (s, 6H, COOCH$_3$), 3.29-3.69 (m, 10H, —CH$_3$, —CH$_2$—).

Example 16

D$_2$O, 400 MHz, δ: 7.41-7.89 (m, 4H, ArH), 5.18 (s, 1H, CH), 2.27-3.92 (m, 39H, —CH$_3$, —CH$_2$—).

Example 17

D$_2$O, 400 MHz, δ: 7.68 (d, J=8.6 Hz, 2H, ArH), 7.44 (d, J=8.6 Hz, 2H, ArH), 5.23 (s, 1H, CH), 3.63 (s, 6H, COOCH$_3$), 3.00-3.91 (m, 20H, —CH$_2$—), 1.40-2.15 (m, 11H, —CH$_3$, —CH$_2$—).

Example 18

CDCl$_3$, 400 MHz, δ: 7.04-7.31 (m, 4H, ArH), 5.53 (s, 1H, CH), 3.70 (s, 6H, COOCH$_3$), 3.27 (s, 3H, N—CH$_3$), 2.47 (s, 6H, CH$_3$).

Example 19

D$_2$O, 400 MHz, δ: 7.46-7.52 (m, 1H, ArH), 7.19-7.35 (m, 3H, ArH), 5.48 (s, 1H, CH), 3.70-3.81 (m, 10H, COOCH$_3$, —CH$_2$—), 3.10-3.52 (m, 15H, —CH$_3$, —CH$_2$—), 2.00-2.30 (m, 8H, —CH$_2$—).

Example 20

D$_2$O, 400 MHz, δ: 7.46-7.53 (m, 1H, ArH), 7.19-7.35 (m, 3H, ArH), 5.48 (s, 1H, CH), 3.20-4.32 (m, 24H, —CH$_3$, —CH$_2$—).

Example 21

D$_2$O, 400 MHz, δ: 7.47-7.53 (m, 1H, ArH), 7.19-7.35 (m, 3H, ArH), 5.48 (s, 1H, CH), 3.03-3.84 (m, 39H, —CH$_3$, —CH$_2$—).

Example 22

D$_2$O, 400 MHz, δ: 7.47-7.53 (m, 1H, ArH), 7.37-7.27 (m, 2H, ArH), 7.19-7.24 (m, 1H, ArH), 5.48 (s, 1H, CH), 3.80 (s, 6H, COOCH$_3$) 3.28-3.49 (m, 11H, —CH$_2$—, —CH$_3$) 3.02 (s, 12H, —CH$_3$).

Example 23

D$_2$O, 400 MHz, δ: 7.51 (d, J=8.3 Hz, 2H, ArH), 7.28 (d, J=8.6 Hz, 2H, ArH), 5.07 (s, 1H, CH), 3.67 (s, 6H, COOCH$_3$), 3.14-3.59 (m, 11H, —CH$_2$—, —CH$_3$), 2.87 (s, 12H, —CH$_3$).

Example 24

CDCl$_3$, 400 MHz, δ: 6.64-6.73 (m, 2H, ArH), 6.55-6.63 (m, 1H, ArH), 5.17 (s, 1H, CH), 3.75 (s, 6H, COOCH$_3$), 3.21 (s, 3H, N—CH$_3$), 2.52 (s, 6H, CH$_3$).

Example 25

D$_2$O, 400 MHz, δ: 6.71-6.82 (m, 3H, ArH), 5.07 (s, 1H, CH), 3.73 (s, 6H, COOCH$_3$), 3.16-3.39 (m, 11H, —CH$_2$—, —CH$_3$), 2.92 (s, 12H, —CH$_3$).

Example 26

D$_2$O, 400 MHz, δ: 6.76-6.86 (m, 3H, ArH), 5.07 (s, 1H, CH), 3.78 (s, 3H, COOCH$_3$), 3.75 (s, 3H, COOCH$_3$), 3.23-3.37 (m, 7H, —CH$_2$—, —CH$_3$), 2.97 (s, 6H, —CH$_3$), 2.46 (s, 3H, —CH$_3$).

Example 27

CDCl$_3$, 400 MHz, δ: 7.39 (d, J=8.6 Hz, 2H, ArH), 7.21 (d, J=8.6 Hz, 2H, ArH), 5.08 (s, 1H, CH), 3.67 (s, 6H, COOCH$_3$), 3.14 (s, 3H, N—CH$_3$), 2.99-3.11 (m, 2H, —CH$_2$—), 2.71-2.84 (m, 2H, —CH$_2$—), 1.06-1.12 (m, 6H, CH$_3$).

Example 28

CDCl$_3$, 400 MHz, δ: 7.45 (d, J=8.6 Hz, 2H, ArH), 7.28 (d, J=8.6 Hz, 2H, ArH), 5.18 (s, 1H, CH), 5.01-5.09 (m, 1H, CH), 3.71 (s, 3H, COOCH$_3$), 3.19 (s, 3H, N—CH$_3$), 2.44-2.53 (m, 6H, —CH$_3$), 1.18-1.33 (m, 6H, CH$_3$).

Example 29

CDCl$_3$, 400 MHz, δ: 7.45 (d, J=8.6 Hz, 2H, ArH), 7.28 (d, J=8.6 Hz, 2H, ArH), 5.18 (s, 1H, CH), 3.73 (s, 3H, COOCH$_3$), 3.20 (s, 3H, N—CH$_3$), 2.52 (s, 3H, CH$_3$), 2.45 (s, 3H, CH$_3$), 1.50 (s, 9H, CH$_3$).

Example 30

D$_2$O, 400 MHz, δ: 7.71 (d, J=8.6 Hz, 2H, ArH), 7.46 (d, J=8.6 Hz, 2H, ArH), 5.26 (s, 1H, CH), 3.86 (s, 6H, COOCH$_3$), 2.85-3.76 (m, 21H, —CH$_2$—, —CH$_3$), 1.39-2.17 (m, 6H, —CH$_3$).

Example 31

D$_2$O, 400 MHz, δ: 7.67 (d, J=8.6 Hz, 2H, ArH), 7.43 (d, J=8.6 Hz, 2H, ArH), 5.22 (s, 1H, CH), 2.93-4.14 (m, 28H, COOCH$_3$, —CH$_2$—, —CH$_3$).

Example 32

CDCl$_3$, 400 MHz, δ: 7.49 (d, J=8.6 Hz, 2H, ArH), 7.33 (d, J=8.6 Hz, 2H, ArH), 5.26 (s, 1H, CH), 4.16-4.25 (m, 2H, —CH$_2$—), 3.23 (s, 3H, N—CH$_3$), 2.54 (s, 6H, CH$_3$), 1.24-1.34 (m, 3H, —CH$_3$).

Example 33

CDCl$_3$, 400 MHz, δ: 7.52 (d, J=8.6 Hz, 2H, ArH), 7.36 (d, J=8.6 Hz, 4H, ArH, —CH—), 4.98 (s, 1H, CH), 4.03-4.20 (m, 4H, —CH$_2$—), 3.01-3.08 (m, 1H, —CH—) 1.18-1.26 (m, 6H, CH$_3$), 0.85-1.01 (m, 4H, —CH$_2$—).

Example 34

CDCl$_3$, 400 MHz, δ: 7.26-7.55 (m, 11H, ArH, —CH—), 5.02 (s, 1H, CH), 4.63 (s, 2H, —CH$_2$—), 4.01-4.18 (m, 4H, —CH$_2$—), 1.18-1.26 (m, 6H, CH$_3$).

Example 35

CDCl$_3$, 400 MHz, δ: 7.52 (d, J=8.6 Hz, 2H, ArH), 7.36 (d, J=8.6 Hz, 2H, ArH), 5.28 (s, 1H, CH), 3.74 (s, 3H, —CH$_3$), 3.23 (s, 3H, —CH$_3$) 2.53 (s, 6H, —CH$_3$).

Example 36

DMSO-d$_6$, 400 MHz, δ: 11.95 (s, 2H, COOH), 7.57 (d, J=8.6 Hz, 2H, ArH), 7.33 (d, J=8.6 Hz, 2H, ArH), 5.11 (s, 1H, CH), 3.17 (s, 3H, —CH$_3$), 2.41-2.55 (m, 6H, —CH$_3$).

Example 37

CDCl$_3$, 400 MHz, δ: 7.52 (d, J=8.6 Hz, 2H, ArH), 7.45 (d, J=8.6 Hz, 2H, ArH), 7.30 (s, 1H, CH), 7.23 (s, 1H, CH), 5.00 (s, 1H, CH), 4.03-4.20 (m, 4H, —CH$_2$—), 3.31 (s, 3H, —CH$_3$), 1.18-1.26 (m, 6H, CH$_3$).

Reference Example 38

CDCl$_3$, 400 MHz, δ: 7.09-7.52 (m, 12H, ArH, —CH—), 4.94 (s, 1H, CH), 4.61 (s, 2H, —CH$_2$—), 4.01-4.18 (m, 4H, —CH$_2$—), 1.14-1.24 (m, 6H, CH$_3$).

Reference Example 39

DMSO-d$_6$, 400 MHz, δ: 11.74 (s, 2H, COOH), 7.29-7.49 (m, 7H, ArH, —CH—), 7.15-7.23 (m, 5H, ArH), 4.77 (s, 2H, —CH$_2$—), 4.67 (s, 1H, CH).

Example 52

Resolution (1) of Compound of Ex. 14

1.5 mmol of dimethyl 2-(2-dimethylaminoethyl)-1,6-dimethyl-4-(4-trifluoromethyl-phenyl)-1,4-dihydropyridine-3,5-dicarboxylate was dissolved in methanol and 0.5 equivalent of (+)-O,O'-dibenzoyl-D-tartaric acid was added. After a short heating the mixture was evaporated off and the residue was crystallized from diisopropylether-ethyl acetate mixture. The resulting crystals were recrystallized from ethyl acetate. The dihydropyridine base was obtained after NaHCO$_3$ treatment. $[\alpha]_D^{25}$=−59.8 (c=0.5 in methanol)
Its HCl salt was recrystallized from methanol-diethyl ether yielding compound Ex. No.: 14/I, mp 210-212° C., $[\alpha]_D^{25}$=−65.8 (c=0.5 in methanol).
The mother liquor was evaporated and basified with NaHCO$_3$ yielding compound Ex. No.: 14/II $[\alpha]_D^{25}$=+39.6 (c=0.5 in methanol)

Example 53

Resolution (2) of Compound of Ex. 14

It was made similarly to Resolution (1) using (−)-O,O'-dibenzoyl-L-tartaric acid. Mp of the HCl salt 200-203° C., $[\alpha]_D^{25}$=−69 (c=0.5 in methanol). The NMR (400 MHz, CDCl$_3$) spectra of the enantiomers are similar to that for racemic substance.

Biological Examples

Example 54

Hsp Co-Inducing Activity

The Hsp co-inducing effect of the compounds on stress response was tested on B16 mouse melanoma and SHSY5Y human neuroblastoma cell lines stably transfected with Hsp promoter probing plasmids. This kind of promoter probing, using the promoter region of a given gene conjugated with fluorescent protein is used as a best and fastest test system for finding drugs which modulate the activity of the gene followed by the given promoter (Wyshocka et al., Mol. Cel. Biochem. 215:153-156, 2000).

The Hsp encoding genes are transactivated through the binding of HSF to the heat shock element found on the DNA upstream of the Hsp genes, in the so called promoter region. In the absence of heat stress, the heat shock factors are present as monomers. Upon heat stress, however, the heat shock factors form trimers, which are the active components, able to bind to heat shock elements. Once HSF is bound to the heat shock element in the promoter of Hsp genes, the gene following the promoter region is transcriptionally active.

Reporter plasmids, containing the Hsp70 and/or Hsp25 promoter conjugated to either YFP or GFP (yellow or green fluorescent protein), were stably transfected into the cells and the expression of YFP or GFP was followed by flow cytometry. Cells were either kept at 37° C. or exposed to heat shock at 42° C. for 1 hour followed by a 16 hour recovery period at 37° C. in the presence or absence of different concentrations of the test compound. After recovery the expression of YFP or GFP which is in straight correlation with the promoter activity of Hsp70 or Hsp27 genes was followed by measuring the fluorescence intensity of the cells by flow cytometry. Fluorescence intensity is in straight correlation with the amount of fluorescent protein (GFP or YFP) produced under the control of hsp promoter. The mean fluorescence intensity of YFP or GFP produced is shown as "Hsp promoter activity".

The Hsp modulating activity for several compounds of the invention are summarised in the following Table 3 and are presented on FIGS. 1 to 10.

TABLE 3

Hsp modulating activity of the compounds

| Example No. | Hsp70 modulation | Other in vitro effects | In vivo efficacy |
|---|---|---|---|
| 1 | +* | 0**** | Insulin resistance |
| 2 | + | 0 | nd*** |
| 3 | + | 0 | nd |
| 4 | −−** | 0 | nd |
| 6 | −−** | 0 | nd |
| 7 | + | 0 | nd |
| 8 | + | 0 | nd |
| 10 | + | 0 | nd |
| 11 | ++ | Hsp25+ | nd |
| 12 | − | 0 | nd |
| 14 | ++ | 0 | Cancer mono- |
| 14/I | +++ | | therapy☑ |
| 14/II | ++ | | |
| 16 | ++ | 0 | nd |
| 17 | +++ | Hsp25 0 | Cancer mono-therapy☑ |
| 23 | +++ | Hsp25 0 Hsp27 0 lysosome destabilization | UVB protection ALS Alzheimer☑ |
| 24 | + | 0 | nd |
| 25 | + | 0 | nd |
| 26 | + | 0 | nd |
| 27 | −−− | HSP25−−− cancer combination therapy) | nd |
| 30 | + | 0 | nd |
| 32 | + | 0 | nd |
| 33 | + | 0 | nd |
| 34 | + | 0 | nd |
| 37 | + | 0 | nd |
| 38 | + | 0 | nd |
| 39 | − | 0 | nd |
| 40 | + | 0 | nd |
| 41 | + | 0 | nd |
| 42 | + | 0 | nd |
| 44 | + | 0 | nd |
| 45 | + | 0 | nd |

TABLE 3-continued

Hsp modulating activity of the compounds

| Example No. | Hsp70 modulation | Other in vitro effects | In vivo efficacy |
|---|---|---|---|
| 47 | + | 0 | nd |
| 49 | +++ | 0 | nd |

+* co-inducing activity
−** silencing activity
0****: with the experimental methods applied no other HSP modulating effects could be identified
nd*** no data FIG. 1 demonstrates that application of compound of Example 23 (20 μM) results in approximately 20 times higher induction of Hsp70 gene activity when SHSY5Y cells were exposed to elevated temperature (42° C.) in the presence of the compound. This compound is a strong concentration dependent co-inducer for Hsp70 stress protein as it does not affect the activity of the promoter of the hsp70 gene at 37° C. in the same cell line. The fluorescence intensity of YFP produced as a result of Hsp70 promoter activity was measured by flow cytometry.

Figure 2:
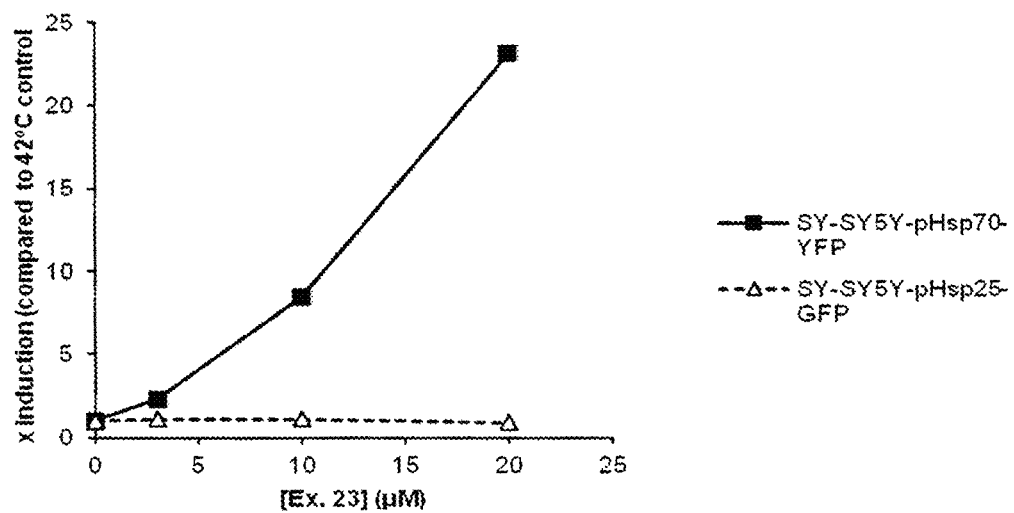
FIG. 2 Selective co-inducing activity of compound of Ex. 23 for Hsp70 over other Hsps FIG. 3 Hsp25 co-inducing activity of compound of Ex. 11 on SHSY5Y cells FIG. 4 Hsp70 silencer activity of compound Ex. 27 on B16 F-10 melanoma cells FIG. 5 Fasting plasma glucose level (A) and Hsp70 protein level (B) (measured with Western blot) of brown adipose tissue in Zucker obese rat treated with compound of Ex. 1

Selectivity of the Hsp70 co-inducing activity of compound of Example 23 is shown on FIG. 2: while compound of Example 23 induces a 23 fold increase in HSP70 expression, it has no effect on the expression of Hsp25 in SHSY5Y cells. This compound is a strong and selective co-inducer for Hsp70 stress protein as it does not affect the activity of the promoter of the hsp25 gene in the same cell line. The fluorescence intensity of GFP and YFP to the values measured in cells treated at 42° C. without the compound.

Figure 3:
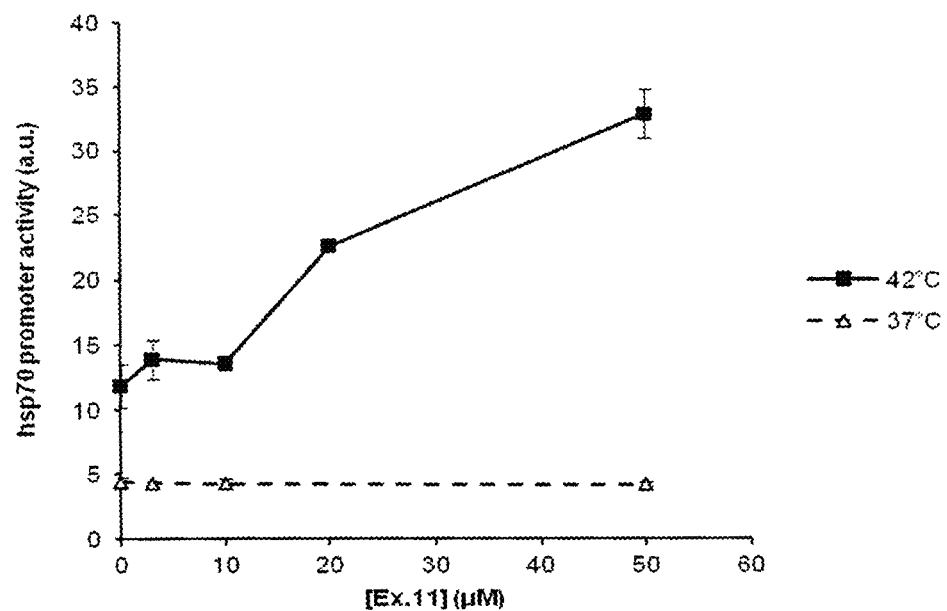

Selectivity of the Hsp25 co-inducing activity of compound of Ex. 11 is shown on FIG. 3. This compound is a strong, concentration dependent co-inducer for Hsp25 stress protein as it does not affect the activity of the promoter of the Hsp25 gene at 37° C. in the same cell line. The fluorescence intensity of GFP produced as a result of Hsp25 promoter activity was measured by flow cytometry.

Figure 4:
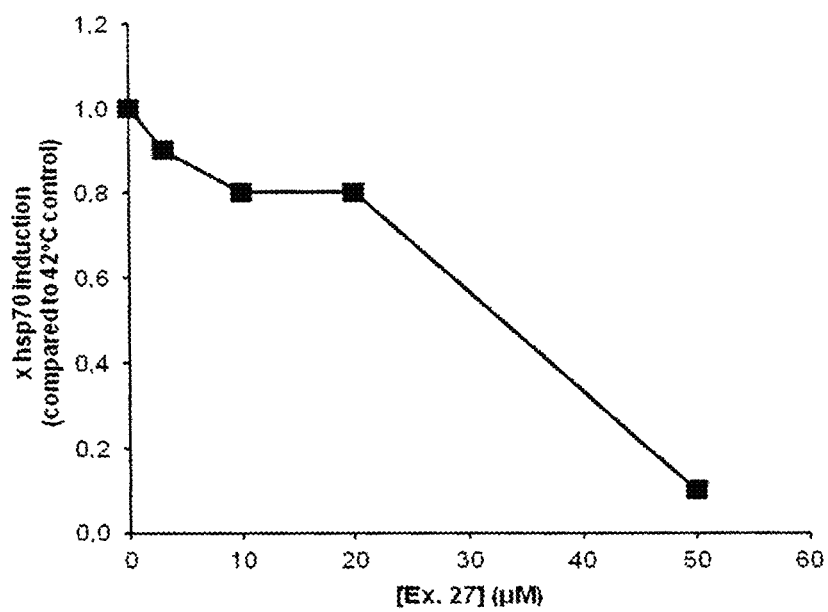
Figure 5:
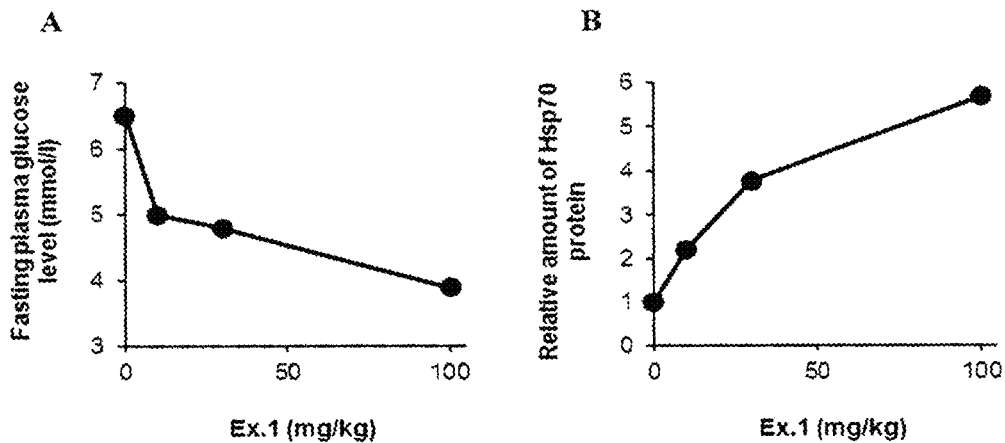

Some of the compounds are Hsp70 selective stress protein response silencers as shown on FIG. 4. Compound of Ex. 27 is a strong concentration dependent silencer for stress induced Hsp70 gene activity. The fluorescence intensity of YFP produced as a result of Hsp70 promoter activity was measured by flow cytometry.

All above results reveal the unique properties of the compounds of invention i.e., they act only in cells under stress (i.e., when affected by specific and nonspecific stimulus events that disturb its equilibrium and may lead to pathological changes) and they possess a selective activity towards the different type of Hsps. The observed Hsp modulating activity of the compounds of invention is independent from the $Ca^{2+}$ channel antagonist effect responsible for the antihypertensive activity of the known 1,4-dihydropyridines. For example we found an index of $EC_{50}$ HSP-modulating/$Ca^{2+}$ antagonist effect equal about 1 for Nilvadipine which corresponds to the data that the effective neuroprotective dose for Nilvadipine (8 mg daily; U.S. Pat. No. 8,236,346 B2) is equal to its antihypertensive dose (Int. J. Clinical Pharmacol. Ther., 1997, 35:195-203), whereas the index of $EC_{50}$ Hsp modulating/$Ca^{2+}$ antagonist effect for the compounds of invention is at least beyond 10. Thus, the possible separation of an antihypertensive effect permits to provide selected compounds which may be administered when treating pathophysiological conditions mediated by Hsps, including for example neurodegenerative diseases, cancer, metabolic syndromes, diabetes, obesity, inflammation and skin diseases in doses varying in a large scale without the danger causing hypotension.

Methods

Promoter Probing Experiments

Cells were homogenously distributed on 6-well plates in $1 \times 10^5$ cells/well density. B16-pHsp25-GFP and B16-pHsp70-YFP melanoma cells were grown in RPMI-1640 medium supplemented with 10% Fetal bovine serum (FBS), penicillin (200 units/ml), streptomycin (200 μg/ml) and 2 mM L-Glutamine. For maintaining the SH-SY5Y-pHsp25-GFP and SH-SY5YpHsp70-YFP neuroblastoma cell lines Dulbecco's modified Eagle's medium (DMEM-F-12) containing 10% FBS, 2 mM L-Glutamine, penicillin (200 units/ml), streptomycin (200 μg/ml) and MEM non-essential amino acids were used. Before the treatments both cell lines were incubated at 37° C. in a saturated humidity atmosphere containing 95% air and 5% CO2. After 24 h incubation cells were pretreated with compounds of the invention in four different concentrations (usually in 3; 10; 20 and 50 μM) 30 min before the heat shock at 42° C. for 1 h and then incubated further at 37° C. for 16 h (recovery period). After this procedure cells were trypsinized and suspended in 500 μl serum-free DMEM-F12 medium. The changes in cells' fluorescence were detected using BD FACSCalibur flow cytometer.

Western Blot Analysis

SY-SY5Y and B16 cells were extracted in NP-40 lysis buffer (PBS pH 7.4, 1% protease inhibitor coctail and 1% Triton X-100). The cell extracts were then constantly agitated at 4° C. for 2 h. The cell extracts were centrifuged at 12000×g for 30 min and supernatants were saved. After the protein concentration measurement 15 μg of total protein was separated by sodium dodecyl sulfate-polyacrylamide gel electrophoresis (SDS-PAGE) under reducing conditions according to the method of Laemmli. Proteins were blotted onto PVDF membrane. The blot was incubated overnight at 4° C. in the presence of mouse α-Hsp25, α-Hsp70, α-Hsp60 és α-Hsp90 monoclonal antibodies diluted in PBS. Then, the membrane was washed three times in PBS-0.05% Tween and incubated for 1 h in peroxidase-conjugated anti-mouse IgG antibody diluted 1:50000 in PBS containing 3% non-fat dry milk. The immune complexes were detected with chemo-luminescent substrate of peroxidase according to the supplier's instructions. Images taken from the membranes were analyzed using AlphaEase FC software.

Cytotoxicity Test

Cells were homogenously distributed on 96-well plates in $5 \times 10^3$ cells/well density then incubated for 24 h at 37° C. On the next day cells were treated with compounds of the invention in 100 nM-200 μM concentration range for 24 h. The viability of the cells were measured using alamarBlue® assay kit according to the supplier's instructions.

Example 55

Insulin Resistance

Insulin sensitizing activity of the compounds was tested in Zucker obese rat at three doses (10, 30 and 100 mg/kg), 6 weeks old Zucker obese (ZO) rats were adapted for a week before the administration of the compound. The animals were treated once a day for 5 days with compound Ex. 1 with 10, 30 and 100 mg/kg dose by stomach probe. The control group was treated with Klucel solution. The animals were kept in metabolic cage during the experiment, their food and drink consumption, the amount of urine and faeces was determined daily.

At the end of the treatment period the animals were fasted for 16 hours, the fasting plasma glucose level was determined. At the end the animals were sacrificed and different organs were taken for Hsp measurement.

Zucker obese rat treated with compound of Ex. 1 showed an improved fasting plasma glucose level (A) and elevated Hsp70 amount in brown adipose tissue (B) in a concentration dependent manner (FIG. 5A, FIG. 5B). Hsp70 level of brown adipose tissue and fasting glucose level in Zucker obese rat treated with compound of Ex. 1 shows correlation with the applied drug concentration.

Example 56

Neuroprotection

The neuro- and memoryprotective effect of the compounds of invention was studied on wild and APP mutant transgenic mice. These mice express high levels of mutant beta-amyloid and, with increasing age, develop both substantial amyloid plaque load and memory deficits. Spatial memory disfunction [with the Morris water maze (MWM) behavioural task assay] and histological assays (cell density, astroglial response, tau-pathology, amyloid-histology and dendritic spine density) in the hippocampal (HC) region (key area for the memory-function) were performed.

The Morris water navigation task is a behavioral procedure widely used in behavioral neuroscience to study spatial learning and memory. The classic measure of learning is latency, which is the time it takes to find the platform after repeating the task daily.

Materials and Methods

Subjects 16 adult female APP+ transgenic and 16 adult female wild type mice were the subjects of the experiment. The animals were housed in sterile mouse cages with a natural dark/light cycle, they had free access to food and water throughout the experiment. After arrival, the mice were daily gently handled for a week.

Treatment

In the experiment there were four different animals groups: a wild and an APP mutant group treated with either physiological saline (PB) or the compounds of invention (Ex. 23). The animals were daily treated intraperitoneally for 6 months.

Spatial Navigation

Spatial learning and memory were assessed in a circular pool (diameter: 130 cm, height: 60 cm), filled with water ($23\pm1°$ C.) and made opaque with milk.

The pool was divided into four virtual quadrants, an invisible platform (diameter: 10 cm) was submerged every day in the middle of the first quadrant 2 cm below the water surface, around the pool in two side was black curtain in two side white walls, in all side were colourful distal cues.

The animals were i.p injected along the MWM task too. The experiment was an 8-day test and included two parts. In part one on the first 6 days, the platform's position was the same every day. Four different starting points were used, the animals swam every day twice, first from a nearer, and then a farther start position. The animals were placed into the water facing the wall of the pool and were given 90 s to find the platform and 20 s to stay on it. Animals not finding the platform were gently guided and placed on it. In part two on the $8^{th}$ day, after one noswimming day, the platform was taken out from the pool that was the probe trial. The animals were given 60 sec to swim, the start point was the farthest place from the platform position (on this day the animals swam once).

The data were recorded and evaluated automatically by using a video tracking system. The means of the data from total duration in the arena (sec) were used for statistics; they were compared with one-way analysis of variance, followed by Fisher's LSD post hoc test.

Results

Figure 6:
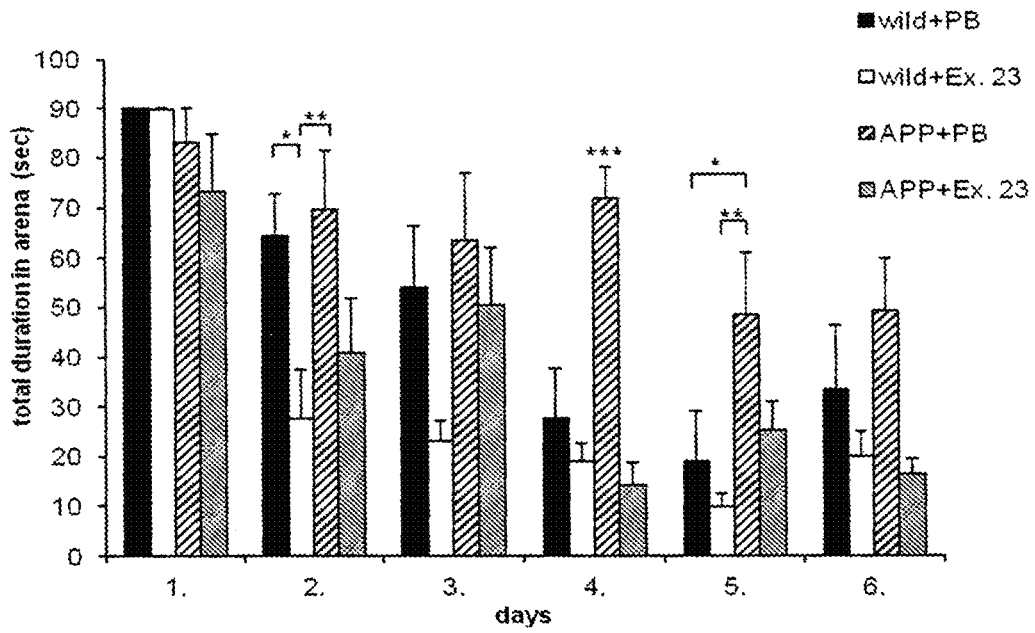
FIG. 6 Shows neuro- and memory protection by compound of Ex. 23 (PB: Physiological saline)

As it is demonstrated on FIG. 6 all groups needed significantly less time to reach the platform on the $4^{th}$ day then the APP+PB group ($F_{32.3}=16.22$; $p=0.001$). Interestingly, the wild+PB group spent significantly more time in the arena then the wild+compound Ex. 23 group ($p=0.001$). The APP+Ex. 23 mice were also better in finding the platform than the wild+PB group ($p=0.001$) and far better than the APP+PB group. This difference is visible on the $5^{th}$ day too ($F_{32.3}=3.76$; $p=0.022$) compared the APP+PB with wild+PB ($p=0.021$) and wild+compound Ex. 23 ($p=0.003$) groups. The tendency was right on the $6^{th}$ day too, there was marginal significance in time spending in the arena between the groups ($p=0.057$), however the Ex. 23 compound treated animals all spent less time in finding the platforms than PB treated animals and the time was similar for wild+PB to APP+compound Ex. 23. There was a significant difference as early as on the $2^{th}$ day ($F_{32.3}=3.75$; $p=0.022$), compared the wild+compound of Ex. 23 treated group to wild+PB ($p=0.017$) or APP+PB group ($p=0.006$) groups. The compound enhances the ability of both the wild type and the memory deficit mutant mice to find the hidden platform in a Morris water maze experiment indicating an improved spatial memory function.

Example 57

Histology

After the Morris water maze task the animals were deeply anesthetized, and transcardialy perfused with 10 ml 4° C. phosphate-buffered saline solution (PBS), followed by 30 ml of 4° C. paraformaldehyde solution (4% in phosphate buffer, pH 7.4). The brains were removed and postfixed for 24 h in the same fixative (4° C.) and subsequently cryoprotected in 30% sucrose solution for 72 h (4° C.). Brains were cut on a cryostat in 30 μm hippocampal coronal sections, and the slices were collected and stored at 4° C. in PBS for free floating immunohistochemistry.

Cresyl-Violet Staining

Cresyl violet staining (Nissl staining) is used for neuronal tissue; the stain binds to the acidic components of the neuronal cytoplasm, showing the number of functioning neurons. Slides were stained into the filtered 1% crezyl violet solution for 5 min. and were dehydrated in 50% 70%, 95%, 2×100% ethanol for 1 minute each. After that slides were placed in xylene for another 10 minutes, and coversliped.

GFAP-Immunhistochemistry

Glial fibrillary acidic protein (GFAP)-immunhistochemistry was utilized for detection of reactive astrogliosis, which is a marker for the inflammatory reaction. The effect was visualised by immunostaining with mouse monoclonal antibody (Chamicon, Billerica, USA) used at 1:500 dilution in PBS (pH 7.4).

Tau-Immunhistochemistry

Neurofibrillary tangles (NTFs) are intraneuronal aggregates; these are abnormal accumulations associated with neurodegenerative diseases. To visualize the presence of these structures, we used for immunostaining human PHF-tau MAb(clone AT100) primer antibody at 1:800 dilution in PBS (pH 7.4).

Amyloid-Immunhistochemistry

For the Aβ immunhistochemistry, rabbit anti-beta 1-42 amyloid primer antibody (WO-2; Genetics Company) at 1:800 dilution was employed. The secondary antibody this time was goat anti-rabbit antibody in 1:200 dilution.

The methodological steps in all three immunohistological techniques were the same. After quenching of endogenous peroxidase activity and a blocking step, the sections were incubated overnight at 4° C. with the primary antibody in the presence of 20% goat serum and Triton X-100 0.2%. On the following day, the sections were washed in PBS and incubated for 1 h at room temperature with the secondary biotinylated goat anti-mouse antibody (Vector Laboratories, Burlingame, Calif., USA, 1:400). The next step was a 1 hour incubation with avidine-biotin complex (Vectastain Elit ABC Kit, Vector Laboratories, Burlingame, Calif., USA; 1:400) and detection with nickel-enhanced 3,3'-diaminobenzidine. After immunostaining and washing, all sections were mounted on gelatin-coated slides, air-dried, dehydrated and coverslipped with DPX mountant for histology (Fluka Bio-Chemika, Buchs, Switzerland).

Golgi Staining

Dendritic spines change their density after a CNS injury, to visualize this effect, we made Golgi staining. After the perfusion we made 100 μm sections from the HC area with vibratome. For Golgi staining methods we used Golgi Stain Kit (FD NeuroTechnologies, USA). The slides were analyzed with confocal light microscopy, we counted dendritic spines 100 μm tong on hippocampal pyramidal cells, and start point was 100 μm farther from the stoma.

Statistics

The data were recorded and evaluated automatically by using a video tracking system. The means of the data from the first swimmings were used for statistics.

For histological analyses HistoQuant program made the counting, except the dendritic spine density.

The data were compared with one-way analysis of variance (ANOVA), followed by Fisher's LSD post hoc test.

Results

The histological studies confirm the behavioural results. The cresyl-violet staining shows that compound of Ex. 23 had neuroprotective effect; there were more alive neurons in compound of Ex. 23 treated animals compared with negative control group, and the result of tau-immunohistochemistry was similar: compound of Ex. 23 could inhibit the taupathology, the APP mutant compound of Ex. 23 treated group was in the control rate. The Golgi staining shows also interesting result, like in Morris water maze, the spine density was the highest in the APP mutant compound of Ex. 23 treated group, so we can suppose based on this data, that compound of Ex. 23 somehow can inhibit the spine loss, or had an effect on the neurons, that are in toxic area, to stop degeneration.

Example 58

Neuroprotection (ALS)

Amyotrophic lateral sclerosis (ALS) is a fatal neurodegenerative disease, caused by the death of motor neurons mainly in the spinal cord. The main form of familiar (genetic or inherited) ALS is caused by the mutation of superoxide dismutase 1 (SOD1) gene, which results in extracellular amyloid-like aggregations and progressive neuronal degenerations. Currently there is no effective treatment available, thus a compound which can significantly delay the progress of the disease is of great interest. The "golden standard" of preclinical ALS drug tests is the use of a specific transgenic mouse strain, which harbors high-copy number of human mutated SOD1 gene, having a mutation of G93A.

The effect of Ex. 23 was investigated on lifespan of G93A ALS mouse strain. A total of 33 transgenic female mice (B6SJL-Tg(SOD1*G93A)1Gur/J) were bred from 4 breeding pairs. The breeding pairs were purchased from the Jackson Laboratory (jax.org). The mice were individually housed in an IVC rack. Standard food pellets and water was available ad libidum. Body weight was monitored daily. The compound Ex. 23 was freshly dissolved in saline every day, and was administered daily intraperitoneally at the onset of symptoms in 10 mg/bwkg. Symptom onset was determined according to ALS-TDI neurological score. Mice treated with Ex. 23 lived longer (FIG. 10) than untreated mice (mean survival 143±3 days; n=8 and 132±3 days; n=25, respectively).

Example 59/1

Anticancer Activity

The anticancer activity was tested in C57Bl/6 mouse (B6), the best known syngeneic mouse model of experimental metastatic melanoma. C57Bl/6 mice injected with B16 melanoma cells subcutaneously or intramuscularly develop primary tumors that, in a part of the recipients, give rise to lung metastases. When the B16 cells are injected intravenously via the tail vein, a fraction of the tumor cells homes directly in the lung, where they develop into multiple independent tumor nodules termed "experimental metastases". Although lung tumors are the most prominent, brain, liver and kidney tumors are also detectable in intravenously injected mice. Since the behavior of the tumor-bearing mice is quite uniform, the model is suitable for simultaneous testing of high numbers of drug candidates in a limited number of experimental animals.

The in vivo tumor experiments were performed with cultured B16 cells that were previously re-isolated from lung metastatic nodules, therefore their metastatic potential was kept optimal. The tumor cells liberated from the tumor mass by trypsin digestion were expanded in cell culture and stored in aliquots in liquid nitrogen, while the number of in vitro passages was kept to a minimum. In the experiments, B6 mice were injected with 100 000 B16 melanoma cells i.v. via the tail vein. The drug candidates were dissolved in physiological saline then they were administered i.p. in a volume of 100 ul. Daily treatment of tumor bearing mice started at day 7 after the tumor injection. The body weight of the mice was measured at day 1, 7, 14 and 21. The survival of the tumor bearing mice was recorded daily. All experiments were performed in accordance with national and European animal welfare guidelines. To prevent unnecessary suffering, moribund mice were euthanized.

The first death in the control group was observed at day 15, the last control mouse died at day 32. The mean survival time was 25.25+/−4.13 days, the median survival time was 25.5 days (n=12). The moribund mice autopsied had typically dozens of lung metastasis nodules; in the last one or two days preceding their death some of them showed neurological defects (coordination problems) probably caused by brain metastasis. Treatment with compound of Ex. 14 at 10 mg/kg did not produce drug-related mortality or weight loss. Daily treatment with compound of Ex. 14 from day 7 to day 29 resulted in statistically significant prolongation of survival. Mean survival time has increased from 25.25+/−4.13 days to 29.91+/−3.78 days, $p<0.01$, two-tailed t-test. Increase in life span=18%.

Figure 8:
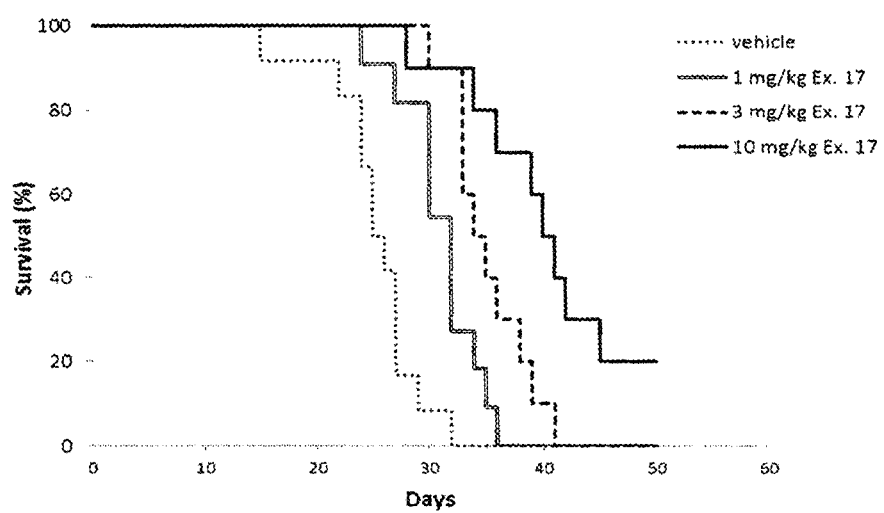

Treatment with compound of Ex. 17 at 10 mg/kg did not produce drug-related mortality and statistically significant drug related weight loss ($LD_{50}$=150 mg/kg). Daily treatment with compound of Ex. 17 from day 7 to day 18 resulted in statistically significant, dose-dependent prolongation of survival (FIG. 8). Mean survival times of mice treated in three different concentrations of Ex 17 are as follows: 1 mg/kg: 31.0+/−3.7 days, p<0.001, two-tailed t-test; 3 mg/kg: 35.55+/−3.80 days, p<0.001, two-tailed t-test; 10 mg/kg: 38.10+/−10.45 days, p<0.001, two-tailed t-test or non-Mann-Whitney non-parametric test. Increases in life span are 23.1%, 40.8% and 53.7%, respectively.

The observed antitumor effect is very pronounced considering the high resistance of melanomas, including the B16 melanoma. Antitumor agents applied in conventional chemotherapy are non-selectively cytotoxic. This sets limits to their use because they are toxic to proliferating healthy cells of various organs and thus produce serious unwanted effects. In contrast, compounds of the invention have no effect on healthy cells, which is a clear advantage in their potential therapeutic use.

Example 59/2

Anticancer Activity—Combination Therapy

Chemotherapy drugs are often more effective when given in combination (combination chemotherapy). The rationale for combination chemotherapy is to use drugs that work by different mechanisms of action, thereby decreasing the likelihood that resistant cancer cells will develop. When drugs with different effects are combined, each drug can be used at its optimal dose that does not cause intolerable side effects. Ex. 27 compound significantly potentiated vincristine (VR) cytotoxicity as demonstrated by a reduction of VR $IC_{50}$ ($IC_{50}$: concentration of drug required for 50% inhibition of cell growth) compared to VR treatment alone in B16F10 melanoma cells. Ex 27 administered at 10 μM decreased the $IC_{50}$ of VR from 1.3 nM to 0.4 nM. The advantage of Ex27 treatment that it has no Ca antagonist effect, therefore it can be applied without unwanted antihypertensive side effects.

Example 59/3

Anticancer Activity—Lysosomal Destabilization

Figure 9:
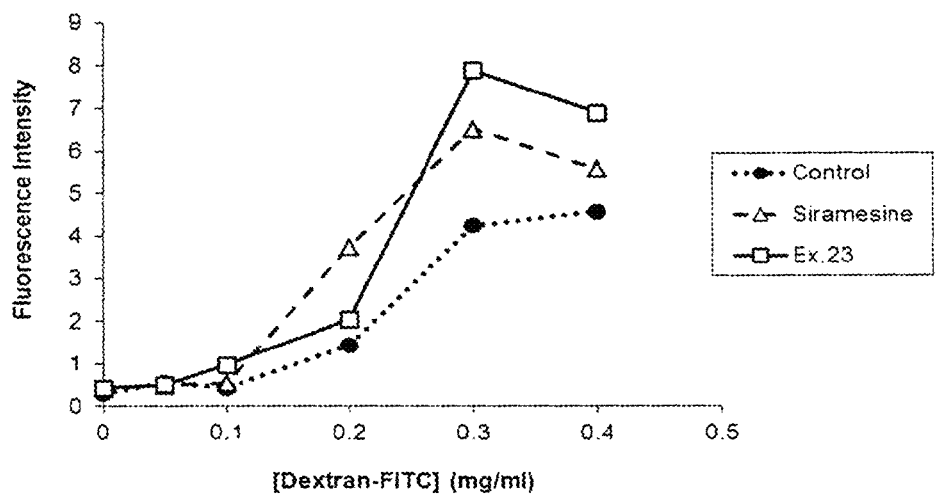
FIG. 9 Effect of compound of Ex. 23 on the lysosomal stability of B16 melanoma cells FIG. 10 The effect compound of Ex. 23 on the lifespan of the ALS model mice The following abbreviations and definitions are used throughout the application.
Figure 10:
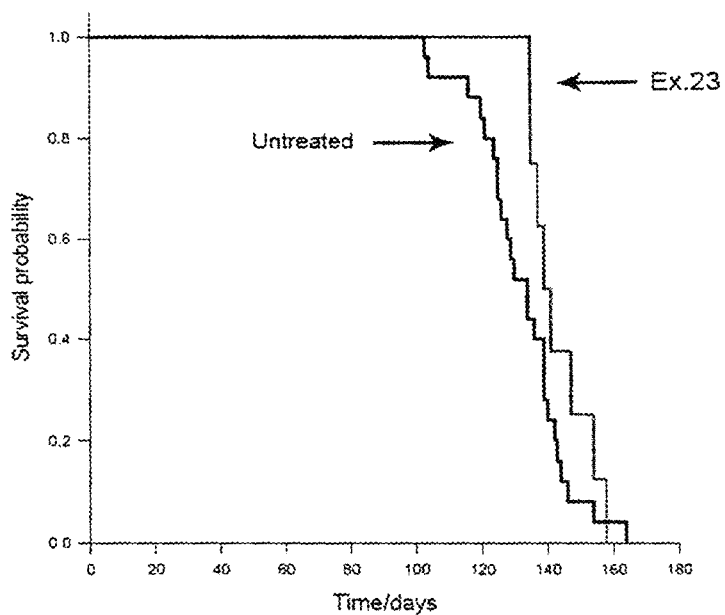

Emerging evidence argues that both classic apoptosis pathways and lysosomal death pathways must be suppressed for effective development and progression of cancer. Tumor invasion and metastasis are associated with altered lysosomal trafficking and increased expression of the lysosomal proteases termed cathepsins. Emerging experimental evidence suggests that such alterations in lysosomes may form an "Achilles heel" for cancer cells by sensitizing them to death pathways involving lysosomal membrane permeabilization and the release of cathepsins into the cytosol (Fehrenbacher and Jaattela, Cancer Res Apr. 15, 2005 65; 2993). Normal cells respond to death stimuli by undergoing caspase-dependent apoptosis, the best characterized form of programmed cell death. In contrast, cancer cells frequently escape spontaneous and therapy-induced caspase activation due to acquired mutations in the apoptotic machinery. Apoptosis-resistant cancer cells are, however, not completely resistant to cell death, but can die via alternative cell death pathways often involving non-caspase proteases such as lysosomal cathepsins. Therefore, development of novel anticancer drugs that can trigger alternative death pathways that are independent of commonly mutated apoptosis-regulating genes is of great importance. Interestingly, transformation and tumor environment enhance the expression of lysosomal cysteine cathepsins. The cathepsins released to the cytosol upon lysosomal membrane permeabilization can trigger caspase-independent and Bcl-2-insensitive apoptosis-like cell death pathways in apoptosis-resistant cells. Siramesine, that is presently being developed as an anticancer drug, destabilizes lysosomes and activates a caspase-independent cell death (Ostenfeld M S, Fehrenbacher N, Hoyer-Hansen M, Thomsen C, Farkas T, Jaattela M. Effective tumor cell death by sigma-2 receptor ligand siramesine involves lysosomal leakage and oxidative stress. Cancer Research. 2005 Oct. 1; 65(19):8975-83; Groth-Pedersen L, Ostenfeld M S, Hoyer-Hansen M, Nylandsted J, Jaattela M. Vincristine induces dramatic lysosomal changes and sensitizes cancer cells to lysosome-destabilizing siramesine. Cancer Research. 2007 Mar. 1; 67(5):2217-25.). As the molecules of the current application also have tumor specific cell killing activity we compared the lysosomotropic activity of Siramesine with Ex. 23. Lysosomal destabilization could be followed by measuring the fluorescence intensity of the pH sensitive FITC-conjugated dextran. Lysosomal pH was determined by allowing the B16F10 melanoma cells to endocytose different amount of FITC-conjugated dextran (40 kDa) (from 10 mg/ml stock) for 24 h. Dextran is actively taken up by the cells and ends up in lysosomes. After a 4-hours chase in fresh medium all dextran was considered to have reached the lysosomes and cells were treated either treated with Siramesine (20 μm) or Ex. 23 (5 μM) for 6 hours. Fluorescence was measured by plate reader using an excitation and emission wavelengths of 485 nm and 538 nm respectively. Ex. 23 treatment resulted in a significantly higher fluorescence intensity reporting an elevated pH that is an increased lysosomal destabilization as compared to Siramesine (FIG. 9).

Example 60

Protection Against UV Induced Skin Damage

To evaluate the effects of systemic administration of Ex. 23 on UVB induced edema 16 SKH-1 hairless mice were divided into two groups of 8 animals each. Group 1 mice (Control) were exposed to 230 mJ/cm² UVB consecutively for 2 days (a total cumulative UVB dose of 460 mJ/cm²), which evoked edema as described by Athar et al. (Tox. Appl. Pharmacol. 195: 370-378, 2004). Group 2 mice received Ex 23. (10 mg/kg) intraperitoneally 30 min before the first UV treatment. The administration of the compound Ex. 23 was repeated 24 and 48 hours later. UVB-induced skin edema was monitored by measuring the increase in dorsal skin thickness using an ultrasound skin scanner (22 MHz). The data show the percent increase in skin thickness compared to the thickness measured before the UVB irradiation.

Figure 7:
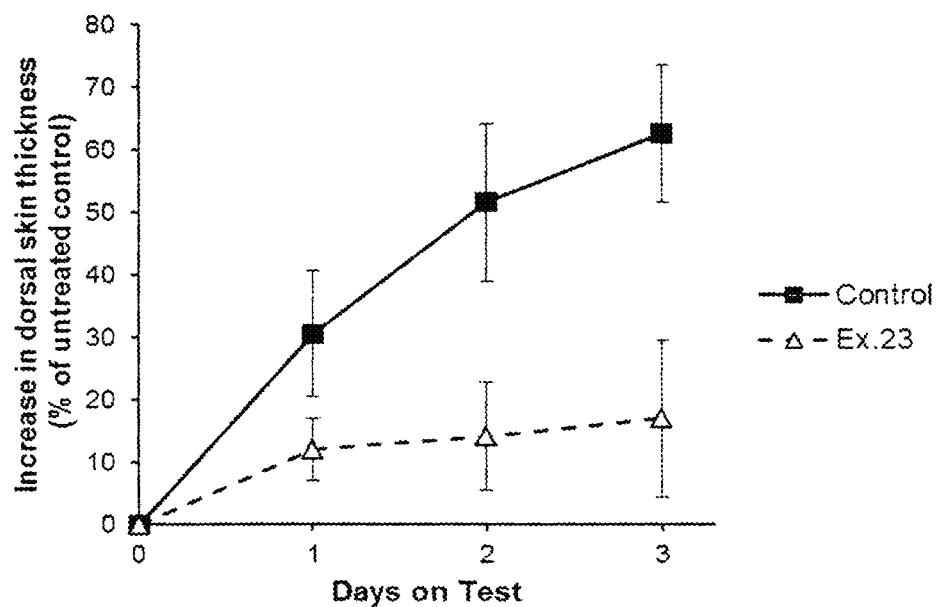
FIG. 7 Effect of compound of Ex. 23 administered systemically on UVB-induced enhancement in skin thickness of SKH-1 hairless mice FIG. 8 Effect of compound of Ex. 17 on the mean survival time of experimental mouse metastatic melanoma model.

The time-dependent effect of Ex. 23 treatment on UVB induced skin edema as measured by an increase in skin thickness is shown in FIG. 7. The UVB irradiation induced a continuous increase in edema during the 3 days observation period. Systemic administration of Ex. 23 substantially protected against edema formation.

The invention claimed is:

1. A compound of formula (I)

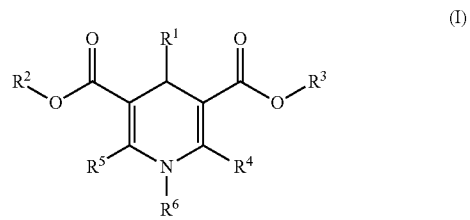

wherein
$R^1$ is a phenyl group optionally substituted with one or two halogens, straight-chained or branched halo$C_{1-6}$ alkyl, $C_{1-6}$alkyl, or $C_{1-6}$alkoxy groups;

$R^2$ and $R^3$ are independently hydrogen or a $C_{1-6}$alkyl group;

$R^4$ is a, $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^5$ is hydrogen; —CN; or a $C_{1-6}$alkyl group optionally substituted with amino, mono- or di($C_{1-6}$ alkyl)amino, or a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; or $R^4$ is hydrogen; —CN; or a $C_{1-6}$alkyl group optionally substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^5$ is a $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^6$ is $C_{1-6}$alkyl, $C_{3-7}$cycloalkyl, $C_{3-7}$cycloalkyl$C_{1-6}$alkyl or aryl$C_{1-6}$alkyl group; or stereoisomers including enantiomers, diastereomers, racemic mixtures, or mixture of enantiomers, or combinations thereof as well as polymorphs, pharmaceutically acceptable salts, or solvates thereof.

2. The compound according to claim 1, wherein $R^1$ is a phenyl group substituted with one or two halogens, or halo$C_{1-6}$alkyl groups;

$R^2$ and $R^3$ are independently a $C_{1-6}$alkyl group;

$R^4$ is a $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^5$ is hydrogen; —CN; or a $C_{1-6}$alkyl group optionally substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; or $R^4$ is hydrogen; —CN; or a $C_{1-6}$alkyl group optionally substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^5$ is a $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^6$ is $C_{1-6}$alkyl group; or stereoisomers including enantiomers, diastereomers, racemic mixtures, or mixture of enantiomers, or combinations thereof; as well as polymorphs, pharmaceutically acceptable salts, or solvates thereof.

3. The compound according to claim 1, wherein $R^1$ is a phenyl group substituted with one or two halogens, or halo$C_{1-6}$alkyl groups;

$R^2$ and $R^3$ are independently a $C_{1-6}$alkyl group;

$R^4$ and $R^5$ are independently a $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^6$ is a $C_{1-6}$alkyl group; or stereoisomers including enantiomers, diastereomers, racemic mixtures, or mixture of enantiomers, or combinations thereof; as well as polymorphs, pharmaceutically acceptable salts, or solvates thereof.

4. The compound according to claim 1, wherein $R^1$ is a phenyl group substituted with one or two halogens, or trifluoro$C_{1-6}$alkyl groups;

$R^2$ and $R^3$ are independently a $C_{1-6}$alkyl group;

$R^4$ and $R^5$ are independently a $C_{1-6}$alkyl group substituted with amino, mono- or di($C_{1-6}$ alkyl)amino, or with a 5 to 12 membered, optionally benzofused, heterocyclic ring attached by nitrogen, optionally comprising additional 1 to 3 N, O, or S heteroatoms, optionally substituted with $C_{1-6}$alkyl or 1 to 3 $C_{1-6}$alkoxy group; and $R^6$ is a $C_{1-6}$alkyl group; or stereoisomers including enantiomers, diastereomers, racemic mixtures, or mixture of enantiomers, or combinations thereof; as well as polymorphs, pharmaceutically acceptable salts, or solvates thereof.

5. The compound according to according to claim 1, wherein $R^1$ is a phenyl group substituted with one or two halogens, or trifluoro$C_{1-6}$alkyl groups;

$R^2$ and $R^3$ are independently a $C_{1-6}$alkyl group;

$R^4$ and $R^5$ are independently a $C_{1-3}$alkyl group optionally substituted with isoquinoline ring attached by nitrogen and optionally substituted with 1 to 3 $C_{1-6}$alkoxy group; and $R^6$ is $C_{1-6}$alkyl group; or stereoisomers including enantiomers, diastereomers, racemic mixtures, or mixture of enantiomers, or combinations thereof as well as polymorphs, pharmaceutically acceptable salts, or solvates thereof.

6. The compound according to claim 1 selected from the group consisting of:

Dimethyl 6-(2-pyrrolidin-1-yl-ethyl)-1,2-dimethyl-4-(4-trifluoromethyl-phenyl)-1,4-dihydropyridine-3,5-dicarboxylate hydrochloride;

Dimethyl 2-(2-dimethylaminoethyl)-1, 6-dimethyl-4-(4-trifluoromethyl-phenyl)-1,4-dihydropyridine-3,5-dicarboxylate hydrochloride;

Dimethyl 1,2-dimethyl-6-(2-morpholin-4-yl-ethyl)-4-(4-trifluoromethyl-phenyl)-1,4-dihydropyridine-3,5-dicarboxylate hydrochloride;

Dimethyl 1-methyl-2,6-bis-[2-(4-methyl-piperazin-1-yl)-ethyl]-4-(4-trifluoromethyl-phenyl)-1,4-dihydropyridine-3,5-dicarboxylate hydrochloride;

Dimethyl 1-methyl-2,6-bis-(2-piperidin-1-yl-ethyl)-4-(4-trifluoromethylphenyl)-1,4-dihydropyridine-3,5-dicarboxylate dihydrochloride;

Dimethyl 4-(2-chlorophenyl)-1-methyl-2,6-bis-(2-pyrrolidin-1-yl-ethyl)-1,4-dihydropyridine-3,5-dicarboxylate dihydrochloride;

Dimethyl 4-(2-chlorophenyl)-1,2-dimethyl-6-(2-morpholin-4-ethyl)-1,4-dihydropyridine-3,5-dicarboxylate hydrochloride;

Dimethyl 4-(2-chlorophenyl)-1-methyl-2,6-bis-[2-(4-methyl-piperazin-1-yl)-ethyl]-1,4-dihydropyridine-3,5-dicarboxylate tetrahydrochloride;

Dimethyl 4-(2-chlorophenyl)-2,6-bis-(2-dimethylaminoethyl)-1-methyl-1,4-dihydropyridine-3,5-dicarboxylate dihydrochloride;

Dimethyl 4-(4-trifuoromethylphenyl)-2,6-bis-(2-dimethylaminoethyl)-1-methyl-1,4-dihydropyridine-3,5-dicarboxylate dihydrochloride;

Dimethyl 4-(3,5-Difluorophenyl)-2,6-bis-(2-dimethylamino-ethyl)-1-methyl-1,4-dihydropyridine-3,5-dicarboxylate dihydrochloride;

Dimethyl 4-(3,5-difluorophenyl)-2-(2-dimethylamino-ethyl)-1,6-dimethyl-1,4-dihydropyridine-3,5-dicarboxylate hydrochloride;

Dimethyl 2,6-diethyl-1-methyl-4-(triflouromethyl-phenyl)-1,4-dihydropyridine-3,5-dicarboxylate;

Dimethyl 2-(2-dimethylamino-ethyl)-1-methyl-6-(2-piperidin-1-yl-ethyl)-4-(4-trifluoromethyl-phenyl)-1,4-dihydro-pyridine-3,5-dicarboxylate dihydrochloride;

Dimethyl 2-(2-dimethylamino-ethyl)-1-methyl-6-(2-morpholin-1-yl-ethyl)-4-(4-trifluoromethyl-phenyl)-1,4-dihydro-pyridine-3,5-dicarboxylate dihydrochloride;

Dimethyl 2-[2-(1,2,3,4-tetrahidroisoquinolin-2-yl)-ethyl]-1,6-dimethyl-4-(4-trifluoromethyl-phenyl)-1,4-dihydropyridine-3,5-dicarboxylate fumarate;

Dimethyl 2-[2-(6,7-dimethoxy-1,2,3,4-tetrahydroisoquinolin-2-yl)-ethyl]-1,6-dimethyl-4-(4-trifluoromethyl-phenyl)-1,4-dihydropyridine-3,5-dicarboxylate hydrochloride;

Dimethyl 2-[2-(6,7-dimethoxy-1,2,3,4-tetrahydroisoquinolin-2-yl)-ethyl]-6-(2-dimethyl-amino-ethyl)-1-methyl-4-(4-trifluoromethylphenyl)-1,4-dihydropyridine-3,5-dicarboxylate dihydrochloride;

Dimethyl 1,2-dimethyl-6-[2-(1,2,4,5-tetrahydrobenzo[d]azepin-3-yl)-ethyl]-4-(4-trifluoromethyl-phenyl)-1,4-dihydropyridine-3,5-dicarboxylate fumarate;

Dimethyl 1,2-dimethyl-6-pyrrolidin-1-ylmethyl-4-(4-trifluoromethylphenyl)-1,4-dihydropyridine-3,5-dicarboxylate hydrochloride;

Dimethyl 2-cyano-1,6-dimethyl-4-(4-trifluoromethylphenyl)-1,4-dihydropyridine-3, 5-dicarboxylate;

Dimethyl 1,2-dimethyl-6-piperidin-1-ylmethyl-4-(4-trifluoromethylphenyl)-1,4-dihydropyridine-3,5-dicarboxylate hydrochloride;

Dimethyl 2-(1,2,3,4-tetrahydro-1H-isoquinolin-2-ylmethyl)-1,6-dimethyl-4-(4-trifluoromethylphenyl)-1,4-dihydropyridine-3,5-dicarboxylate hydrochloride; and Dimethyl 2-cyano-6-(2-dimethylaminoethyl)-1-methyl-4-(4-trifluoromethylphenyl)-1,4-dihydropyridine-3,5-dicarboxylate hydrochloride; or stereoisomers, polymorphs, pharmaceutically acceptable salts, or solvates thereof.

7. The compound according to claim 1 selected from the group consisting of

Dimethyl 2-(2-dimethylaminoethyl)-1,6-dimethyl-4-(4-trifluoromethyl-phenyl)-1,4-dihydropyridine-3,5-dicarboxylate hydrochloride;

Dimethyl 1-methyl-2,6-bis-(2-piperidin-1-yl-ethyl)-4-(4-trifluoromethylphenyl)-1,4-dihydropyridine-3,5-dicarboxylate dihydrochloride;

Dimethyl 4-(4-trifuoromethylphenyl)-2,6-bis-(2-dimethylaminoethyl)-1-methyl-1,4-dihydropyridine-3,5-dicarboxylate dihydrochloride;

Dimethyl 2,6-diethyl-1-methyl-4-(triflouromethyl-phenyl)-1,4-dihydropyridine-3,5-dicarboxylate;

Dimethyl 2-[2-(1,2,3,4-tetrahidroisoquinolin-2-yl)-ethyl]-1,6-dimethyl-4-(4-trifluoromethyl-phenyl)-1,4-dihydropyridine-3,5-dicarboxylate fumarate;

Dimethyl 2-cyano-1,6-dimethyl-4-(4-trifluoromethylphenyl)-1,4-dihydropyridine-3,5-dicarboxylate; and Dimethyl 2-(1,2,3,4-tetrahydro-1H-isoquinolin-2-ylmethyl)-1,6-dimethyl-4-(4-trifluoromethylphenyl)-1,4-dihydropyridine-3,5-dicarboxylate hydrochloride; or stereoisomers, polymorphs, pharmaceutically acceptable salts, or solvates thereof.

8. The compound according to claim 1 or stereoisomers including enantiomers, diastereomers, racemic mixtures, or mixture of enantiomers, or combinations thereof; as well as polymorphs, pharmaceutically acceptable salts, or solvates thereof, are present in an enantiomerically enriched form.

9. A pharmaceutical composition comprising the compound of claim 1 or stereoisomers including enantiomers, diastereomers, racemic mixtures, or mixture of enantiomers, or combinations thereof; as well as polymorphs, pharmaceutically acceptable salts, or solvates thereof, and one or more pharmaceutically acceptable carriers, excipients or combinations thereof.

10. A pharmaceutical composition comprising the compound of claim 1 or stereoisomers including enantiomers, diastereomers, racemic mixtures, or mixture of enantiomers, or combinations thereof as well as polymorphs, pharmaceutically acceptable salts, or solvates thereof in a mixture with a therapeutic agent useful for the treatment of neurodegenerative diseases and one or more pharmaceutically acceptable carriers, excipients, or combinations thereof.

11. A method of modulating heat shock proteins in a patient suffering from a heat shock protein modulated disorder selected from the group consisting of Alzheimer disease, frontotemporal dementia, dementia with Lewy bodies, corticobasal degeneration, progressive supranuclear palsy, prion disorders, multiple system atrophy, amyotrophic lateral sclerosis (ALS or Lou Gehrig's Disease), Parkinson's disease, Huntington's disease, poly-Q related neurodegenerative diseases, multiple sclerosis, hereditary spastic paraparesis, spinocerebellar atrophies, brain cancer related diseases, degenerative nerve diseases, encephalitis, epilepsy, genetic brain disorders, head and brain malformations, hydrocephalus, stroke related diseases, amyloidosis, Friedreich's ataxia, metabolic (diabetes) related diseases, toxin related diseases, and Charcot-Marie-Tooth neuropathy; or any combination thereof, comprising administering to the patient an effective amount of a compound represented by formula (I)

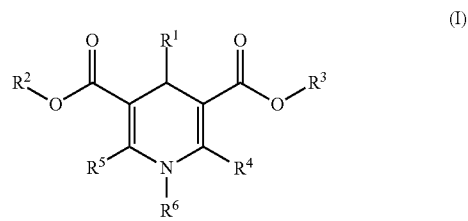

wherein $R^1$ is a phenyl group optionally substituted with one or two halogens, straight-chained or branched haloC$_{1-6}$alkyl, C$_{1-6}$alkyl, or C$_{1-6}$alkoxy groups;

$R^2$ and $R^3$ are independently hydrogen or a $C_{1-6}$alkyl group;

$R^4$ is a $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^5$ is hydrogen; —CN; or a $C_{1-6}$alkyl group optionally substituted with amino, mono- or di($C_{1-6}$ alkyl)amino, or a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; or $R^4$ is hydrogen; —CN; or a $C_{1-6}$alkyl group optionally substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^5$ is a $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^6$ is $C_{1-6}$alkyl, $C_{3-7}$cycloalkyl, $C_{3-7}$cycloalkyl$C_{1-6}$alkyl or aryl$C_{1-6}$alkyl group; or stereoisomers including enantiomers, diastereomers, racemic mixtures, or mixture of enantiomers, or combinations thereof; as well as polymorphs, pharmaceutically acceptable salts, or solvates thereof;

wherein the treatment effectively modulates heat shock proteins and affects only cells under stress and non-stressed healthy cells are unaffected by the treatment.

12. The method according to claim 11, wherein $R^1$ is a phenyl group substituted with one or two halogens, or halo$C_{1-6}$alkyl groups;

$R^2$ and $R^3$ are independently a $C_{1-6}$alkyl group;

$R^4$ is a $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^5$ is hydrogen; —CN; or a $C_{1-6}$alkyl group optionally substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; or $R^4$ is hydrogen; —CN; or a $C_{1-6}$alkyl group optionally substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^5$ is a $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^6$ is $C_{1-6}$alkyl group; or stereoisomers including enantiomers, diastereomers, racemic mixtures, or mixture of enantiomers, or combinations thereof as well as polymorphs, pharmaceutically acceptable salts, or solvates thereof.

13. The method according to claim 11, wherein $R^1$ is a phenyl group substituted with one or two halogens, or halo$C_{1-6}$alkyl groups;

$R^2$ and $R^3$ are independently a $C_{1-6}$alkyl group;

$R^4$ and $R^5$ are independently a $C_{1-6}$alkyl group substituted with amino, mono- or di($C_{1-6}$ alkyl)amino, or with a 5 to 24 membered, optionally fused, heterocyclic ring attached by nitrogen, optionally comprising additional 1 to 3 N, O, or S heteroatoms, and optionally substituted with $C_{1-6}$alkyl or 1 to 3 $C_{1-6}$alkoxy group; and $R^6$ is a $C_{1-6}$alkyl group; or stereoisomers including enantiomers, diastereomers, racemic mixtures, or mixture of enantiomers, or combinations thereof; as well as polymorphs, pharmaceutically acceptable salts, or solvates thereof.

14. The method according to claim 11, wherein $R^1$ is a phenyl group substituted with one or two halogens, or trifluoro$C_{1-6}$alkyl groups;

$R^2$ and $R^3$ are independently a $C_{1-6}$alkyl group;

$R^4$ and $R^5$ are independently a $C_{1-6}$alkyl group substituted with amino, mono- or di($C_{1-6}$ alkyl)amino, or with a 5 to 12 membered, optionally benzofused, heterocyclic ring attached by nitrogen, optionally comprising additional 1 to 3 N, O, or S heteroatoms, optionally substituted with $C_{1-6}$alkyl or 1 to 3 $C_{1-6}$alkoxy group; and $R^6$ is a $C_{1-6}$alkyl group; or stereoisomers including enantiomers, diastereomers, racemic mixtures, or mixture of enantiomers, or combinations thereof; as well as polymorphs, pharmaceutically acceptable salts, or solvates thereof.

15. The method according to according to claim 11, wherein $R^1$ is a phenyl group substituted with one or two halogens, or trifluoro$C_{1-6}$alkyl groups;

$R^2$ and $R^3$ are independently a $C_{1-6}$alkyl group;

$R^4$ and $R^5$ are independently a $C_{1-3}$alkyl group optionally substituted with isoquinoline ring attached by nitrogen and optionally substituted with 1 to 3 $C_{1-6}$alkoxy group; and $R^6$ is $C_{1-6}$alkyl group; or stereoisomers including enantiomers, diastereomers, racemic mixtures, or mixture of enantiomers, or combinations thereof; as well as polymorphs, pharmaceutically acceptable salts, or solvates thereof.

16. The method according to claim 11, wherein the heat shock protein is selected from the group consisting of HSP-70 and HSP-25.

17. The method according to claim 11, which further comprises administering at least one therapeutic agent useful for the treatment of a neurodegenerative disease.

18. The method according to claim 11, which further comprises a thermal treatment simultaneously, separately or sequentially with administering an effective amount of the compound.

* * * * *